(12) United States Patent
Duncan

(10) Patent No.: US 9,212,762 B2
(45) Date of Patent: *Dec. 15, 2015

(54) MULTI-PORT STOPCOCK VALVE AND FLOW DESIGNATING SYSTEM

(71) Applicant: David R. Duncan, Penryn, CA (US)

(72) Inventor: David R. Duncan, Penryn, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/083,825

(22) Filed: Nov. 19, 2013

(65) Prior Publication Data

US 2014/0076431 A1 Mar. 20, 2014

Related U.S. Application Data

(63) Continuation of application No. 12/804,321, filed on Jul. 20, 2010, now Pat. No. 8,584,701.

(51) Int. Cl.
*F16K 37/00* (2006.01)
*F16K 11/085* (2006.01)

(52) U.S. Cl.
CPC ......... *F16K 37/0008* (2013.01); *F16K 11/0853* (2013.01); *Y10T 137/8259* (2015.04); *Y10T 137/8275* (2015.04); *Y10T 137/8309* (2015.04); *Y10T 137/86871* (2015.04)

(58) Field of Classification Search
CPC .............. F16K 37/0008; F16K 11/085; F16K 37/0016; F04B 7/0088
USPC ............ 137/553, 555, 556, 625.47, 876, 887; 116/277; 251/297; 604/248
See application file for complete search history.

(56) References Cited

U.S. PATENT DOCUMENTS

| | | | | |
|---|---|---|---|---|
| 172,568 | A * | 1/1876 | Hughes | 137/625.47 |
| 275,406 | A * | 4/1883 | Parsons | 137/625.47 |
| 373,710 | A * | 11/1887 | Wiswell | 137/625.47 |
| 550,706 | A * | 12/1895 | Worthington | 137/625.47 |
| 706,928 | A * | 8/1902 | Graham | 137/625.47 |
| 828,434 | A * | 8/1906 | Stahl | 137/556 |
| 982,671 | A * | 1/1911 | Hardy | 137/625.47 |
| 1,183,012 | A * | 5/1916 | Kunzer et al. | 137/556 |
| 1,433,092 | A * | 10/1922 | O'Dowd | 137/556.6 |
| 1,633,074 | A * | 6/1927 | De Mott | 137/625.19 |
| 1,990,773 | A * | 2/1935 | Boynton | 137/556.3 |
| 2,229,933 | A * | 1/1941 | Parker | 137/625.11 |
| 2,669,418 | A * | 2/1954 | Brumbaugh | 137/556 |
| 3,048,192 | A * | 8/1962 | Murphy, Jr. | 137/625.47 |
| 3,157,201 | A * | 11/1964 | Littmann | 137/625.47 |
| 3,238,968 | A * | 3/1966 | Pecis | 137/556 |
| 3,505,972 | A * | 4/1970 | Benjamin | 116/277 |

(Continued)

*Primary Examiner* — Craig Schneider
*Assistant Examiner* — Angelisa L Hicks
(74) *Attorney, Agent, or Firm* — Heisler & Associate

(57) ABSTRACT

A stopcock is provided with multiple ports joining multiple fluid conduits leading between fluid sources and fluid destinations. A central hub manifold resides within a valve body supporting the ports, and can rotate relative to the valve body. Fluid flow paths within the central hub are selectively aligned or not aligned with the ports. The stopcock indicates which ports are open by providing marks corresponding with positions of the ports. When the marks are visible, the corresponding ports are open. With different positioning of ports and different configurations of fluid flow paths within the central hub, stopcocks having different numbers of operable positions are provided including two, three, four, six and eight way stopcocks. By providing an axial flow path through a central axis of the central hub intersecting the embedded fluid flow paths within the central hub, still further numbers of operational states are provided.

21 Claims, 16 Drawing Sheets

(56) References Cited

U.S. PATENT DOCUMENTS

| | | | |
|---|---|---|---|
| 3,783,900 A * | 1/1974 | Waldbillig | 137/625.47 |
| 3,834,372 A * | 9/1974 | Turney | 137/625.47 |
| 3,938,553 A * | 2/1976 | Ortega | 137/625.47 |
| 4,494,565 A * | 1/1985 | Sinclair et al. | 137/625.47 |
| 4,593,717 A * | 6/1986 | Levasseur | 137/556.6 |
| 4,850,980 A * | 7/1989 | Lentz et al. | 604/248 |
| 5,540,668 A * | 7/1996 | Wilson et al. | 137/625.47 |
| 5,817,068 A * | 10/1998 | Urrutia | 137/625.47 |
| 6,112,619 A * | 9/2000 | Campbell | 74/553 |
| 8,584,701 B2 * | 11/2013 | Duncan | 137/555 |
| 2005/0092378 A1 * | 5/2005 | Wu | 137/625.47 |

\* cited by examiner

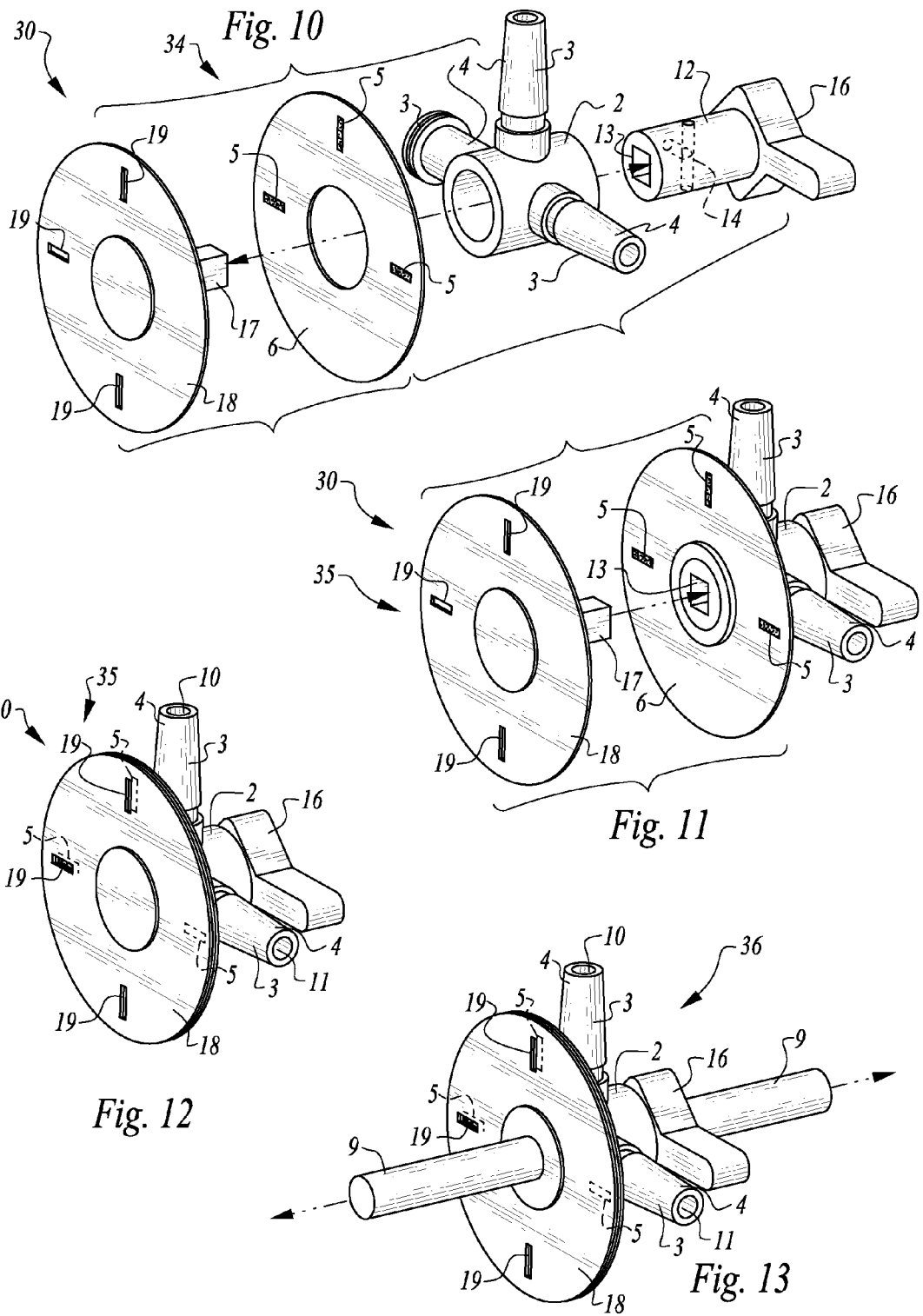

MULTI-PORT STOPCOCK VALVE AND FLOW DESIGNATING SYSTEM

CROSS-REFERENCE TO RELATED APPLICATIONS

This application is a continuation of U.S. patent application Ser. No. 12/804,321 filed on Jul. 20, 2010 and issued as U.S. Pat. No. 8,584,701 on Nov. 19, 2013, which claims benefit under Title 35, United States Code §119(e) of U.S. Provisional Application No. 61/271,422 filed on Jul. 20, 2009.

FIELD OF THE INVENTION

The following invention relates to stopcock type valves for opening and closing fluid pathways. More particularly, this invention relates to stopcocks such as those used in the scientific and medical fields for routing fluids or medication (medicament) into tubing, a device, multiple devices, a patient or any combination thereof. These stopcocks allow for control of fluid flow between various different sources and destinations within a given system.

BACKGROUND OF THE INVENTION

In the scientific fields it is often necessary to manipulate fluid flow through conduits by opening, closing and diverting fluid flow to transport or mix various fluids from various sources. The most common example of this occurs in medicine where medicament (medication or fluid) infusing into a patient via an intravenous or central line) need to be mixed with another infusing medicament in a way that can be manipulated so as to allow or disallow the various infusions as required. These same fluid systems need to allow the practitioner direct sterile access so that a given medicine or fluid may be directly injected, pressure may be directly monitored, or body fluid may be directly removed for sampling.

A common way to accomplish this is through the use of medical stopcocks which are most commonly of the "3 way type" or less commonly "4 way type" (these stopcocks are shown in FIG. 1). These inventions allow ports to be opened or closed as need be to allow or disallow the flow of a given medicament or to allow direct access to the fluid system for the above stated reasons.

A common problem with the use of these 3 and 4 way medical stopcocks is the manipulation or setting of their flow patterns (operable or functional state) based on one's visual assessment. The user must rotate a central hub to align flow through the desired ports based on his or her ability to understand and interpret the functionality of the stopcock. This functionality is most commonly delineated by a single knob which points to the port that is closed, making interpretation of those that are open difficult. This lack of positive delineation leads to misinterpretation of flow patterns with concomitant errors in settings and associated medication errors which may lead to harm or death.

The difficulty in interpreting the flows that will be allowed from a given setting also limits the number of combinations (i.e. 4 way). This limit occurs because with stopcocks that offer more than four combinations (i.e. 4 way), interpretation and manipulation become too complicated and the chances for error increase exponentially. This limits the current technology and requires assembling two or more of the standard stopcocks in series (an arrangement known as a "manifold") if more choices are required. This increases cost, complexity and each stopcock in the chain multiplies the chance of medication errors.

RELEVANT PRIOR ART

U.S. Pat. No. 3,957,082 May 18, 1976 Fuson
U.S. Pat. No. 4,566,480 Jan. 28, 1986 Parham
U.S. Pat. No. 5,144,972 Sep. 8, 1992 Dryden
U.S. Pat. No. 5,156,186 Oct. 20, 1992 Manska
U.S. Pat. No. 4,219,021 Aug. 26, 1980 Fink
U.S. Pat. No. 6,158,467 Dec. 12, 2000 Loo
U.S. Pat. No. 6,230,744 May 15, 2001 Ahrweiler
U.S. Pat. No. 6,418,966 Jul. 6, 2002 Loo
U.S. Pat. No. 6,457,488 Oct. 1, 2002 Loo
U.S. Pat. No. 6,953,450 Oct. 11, 2005 Baldwin
U.S. Pat. No. 7,232,428 Jun. 19, 2007 Inukai All prior art stopcocks, including those listed above are fraught with less than adequate demarcations or indications for whether a given port is in the open or closed position. This problem yields difficulty and error in determining the functionality of the prior art stopcock at any given "setting."

Manska's stopcock (U.S. Pat. No. 5,156,186) does make an attempt to better delineate whether the given port is on or off, by having the "o" in "on" or "off" traverse between the two words, thereby spelling the status of the port it overlies as "on" or "off," but also leaving remnants of words like "ff" over the other ports. This is an improvement over the prior art, but still requires reading, interpreting and assessing each port before the overall functional state can be determined. This modality does not let one interpret at a glance which ports are open and (in use) and is again associated with a greater degree of error than the present invention. This modality (Manska's) only allows up to a "3 way" complexity secondary to these limitations.

Loo's stopcocks (U.S. Pat. Nos. 6,158,467, 6,418,966 and 6,457,488) do include a one sided central fluid path in the hub (on the knob side). This single sided central port only communicates with the outer ports, and does not allow for fluid flow all the way through the hub. Loo's stopcock functionality is very hard to interpret making it difficult to know which ports are open and which are closed. His designs include two separate non-mixing fluid paths which increases the complexity and chance for medication errors, particularly so with the lack of an adequate flow designation system. The optional central fluid flow path of the present invention offers a much needed advantage over this design and others, allowing fluid from an IV or other source to flow through the central hub, independent of the hubs rotated position with respect to the fluid conveyance ports (as is required by the Loo designs), thereby increasing overall functionality, useful ports, and ease in interpreting the functional state. The present invention, for instance, could allow fluid to continue flowing through the central port while all other ports were off (Loo's design has no means to accomplish this). Loo's designs only allow flow from the central port to the peripheral ports.

SUMMARY OF THE INVENTION

With this invention a stopcock is provided which can be both easily manipulated to produce the flow desired between separate ports of the stopcock as well as be readily analyzed, such as by a medical practitioner to determine the current functional or operational state of the stopcock and relative flow therethrough at a glance. The stopcock generally includes a valve body with multiple fluid pathways, such as fluid conveyance ports, joined to the valve body. A central hub defines a preferred form of central manifold which resides within the valve body. This central hub can be rotated within the valve body. Fluid flow paths embedded within the central hub allow for fluid flow therethrough. By aligning ends of the fluid flow paths with the fluid conveyance ports in different orientations, various different ones of the ports are caused to be open or closed to allow or block fluid flow into and out of the stopcock.

Uniquely with this invention, a pair of indicator portions are provided including a first indicator portion and a second indicator portion relating to stopcock operational status. These first and second indicator portions interact with each other to provide this operational status information. One of the indicator portions includes markings generally aligned with the fluid conveyance ports joined to the valve body. The second indicator portion includes a visual barrier which is coupled to the central hub so that the second indicator portion rotates with the central hub. This visual barrier is configured to block markings of the first indicator which are closed and not block markings on the first indicator which correspond with ports which are open. In a preferred form of this invention, the second indicator portion is in the form of a plate with fenestrations therein that are generally aligned with the ends of the fluid flow paths in the central hub. Thus, when these ends of the flow paths of the central hub are aligned with the ports, the fenestrations in the rotating fenestrated plate are aligned with the markings of the first indicator portion, so that the markings can be seen by a user. The user sees a marking adjacent each port which is open and no mark next to each port which is closed. The user can thus readily determine which ports are open and which ports are closed and hence which ports are delivering or receiving fluid within the system in which the stopcock is located.

Various different numbers of ports can be associated with the valve body. Also, various different numbers of ends of fluid paths can be provided along with the central hub. By altering the number of ports associated with the valve body and altering the positions of ends of the flow paths within the central hub, various different numbers of operational states for the stopcock can be provided.

The central hub can optionally include a "flow through" central fluid path preferably extending substantially axially and perpendicular to and/or through the embedded flow paths within the central hub and perpendicular to the ports extending from the valve body. This central fluid conveyance path allows fluid to flow all the way through the center of the hub and is connected with the embedded fluid flow paths which are located within the central hub.

This central fluid conveyance path functions as a distinct flow through fluid route that connects with the open fluid conveyance ports via the connected flow paths within the central hub. This central path adds additional functionality by allowing fluid flow through the center of the stopcock without using the fluid conveyance ports for this purpose, thereby sparing them for other uses. The central fluid conveyance path is not opened or closed by rotation of a central hub as are the ports joined to the valve body. Rather, this central path always allows for continuous fluid flow through it, while rotation of the central hub determines which of the fluid conveyance ports joined to the valve body will be connected to the central flow path. With such a central fluid conveyance path, stopcocks may offer additional functionality with minimal increased complexity. This central fluid path design allows for more complicated stopcocks with increased functionality, while minimizing cost and confusion. A typical appearing four way stopcock with a central fluid path could be easily designed to accommodate eight combinations, whereas to obtain eight combinations previously would have required three prior art stopcocks to be connected in series as a "manifold" of stopcocks. The first and second indicator portions mentioned above would also be present in a preferred embodiment of stopcocks containing a central fluid path.

Objects of the Invention

Accordingly, a primary object of the present invention is to provide a rapid means of assessing the functional status of a stopcock and its attachments.

Another object of the present invention is to provide a stopcock which can be both readily assessed as to its setting status while still being used in a manner familiar to those already trained in the use of prior art stopcocks.

Another object of the present invention is to provide a stopcock which can be simply assessed as to its functional and operational status to minimize the opportunity for errors in utilizing the stopcock, including medication errors.

Another object of the present invention is to provide a stopcock with an intuitive operational status designating system.

Another object of the present invention is to provide a stopcock which allows multiple different fluid flow combinations while still maintaining ease of use and safety.

Another object of the present invention is to provide a stopcock which can replace multiple separate stopcocks arrayed in a manifold, to simplify complex fluid flow arrangement systems.

Another object of the present invention is to provide a stopcock which can be readily interpreted as to its operational state, even in low light conditions, such as by using bright colors or glow in the dark type materials thereon.

Another object of the present invention is to provide a stopcock which can be of simple manufacture and formed of low cost materials, such as by utilization of injection molded plastics.

Another object of the present invention is to provide an indicator for indicating a status of the stopcock which can be configured at various different positions on the stopcock for high visibility in various different fluid flow systems in which the stopcock is included.

Other further objects of the present invention will become apparent from a careful reading of the included drawing figures, the claims and detailed description of the invention.

BRIEF DESCRIPTION OF THE DRAWINGS

FIGS. 10-13 correspond with FIGS. 6-9 except depicting how two indicator plates of the stopcock can be positioned on a side of the stopcock opposite a central control knob as opposed to on the same of the central control knob.

DESCRIPTION OF THE PREFERRED EMBODIMENT

Figure 6:
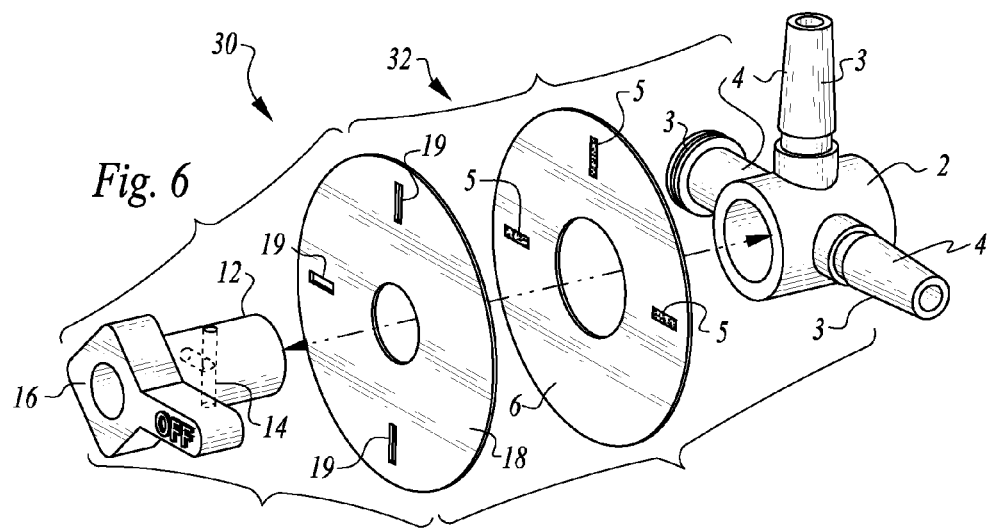
FIGS. 6 and 7 are perspective views of a three or four way stopcock 30 according to this invention, with FIG. 6 fully exploded and FIG. 7 partially exploded.
Figure 7:
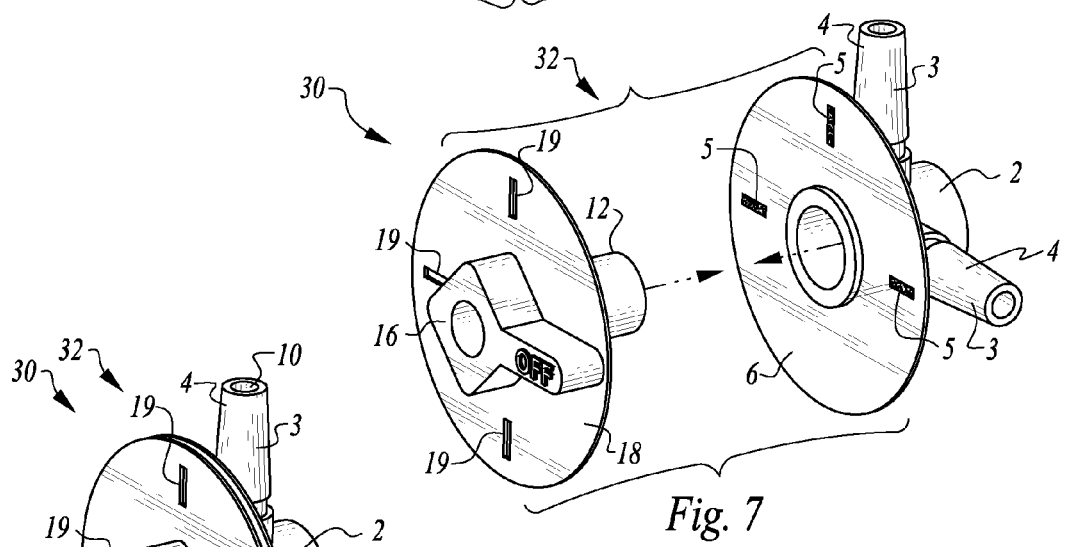

Referring to the drawings, wherein like reference numerals represent corresponding related parts throughout the various drawing figures, reference numeral 1 is directed to a prior art stopcock (FIGS. 1-5). This prior art stopcock 1, as well as the various stopcocks 20, 30, 40, 50, 60, 70, 80, 90 of this invention (FIGS. 6-95) share many common attributes, as well as important distinctions, elucidated herein through reference to exemplary embodiments depicted herein. Through manipulation of these stopcocks, various different fluid conveyance ports 4 joined to a valve body 2 can be either opened or closed for fluid flow therethrough, such as indicated by flow arrows on the drawings associated with the different embodiments. For each embodiment, different views are provided to show the various different positions of a central hub 12 relative to the valve body 2, as well as relative positions of a fixed plate 6 relative to a rotating fenestrated plate 18 which quickly and easily indicates which of the fluid conveyance ports 4 are open through the stopcock.

With particular reference to FIGS. 1-9, basic details common to both prior art stopcocks 1 and the stopcocks 20, 30, 40, 50, 60, 70, 80, 90 of this invention are described. A valve body 2 acts as a housing containing a central hub 12 therein. This valve body 2 has a substantially cylindrical recess. A central hub 12 having a substantially cylindrical form matching that of this recess resides in the recess within the valve body 2. The valve body 2 and central hub 12 can be fitted with seals or manufactured with sufficiently tight tolerances and from appropriate materials to be substantially self-sealing.

The valve body 2 includes a plurality of fluid conveyance ports 4 extending radially from the valve body 2. Each of these ports 4 ends at a terminus 3 most distant from the valve body 2. The terminus 3 of each port 4 typically is configured so that it can be coupled to other fluid conduits, such as medical tubing or directly to sources or destinations of fluids within the system. These sources or destinations can include sensors, medication vials, syringes, a patient interface (e.g. an intravenous catheter), an infusion pump or other fluid handling or processing equipment. The connectors utilized at the terminii 3 can be luer fittings, screw fittings or other forms of fittings common for tubular connectors, including sleeve and clamp connectors and press fit connectors. Ports 4 which are open are identified with the reference numeral 10.

Figure 1:
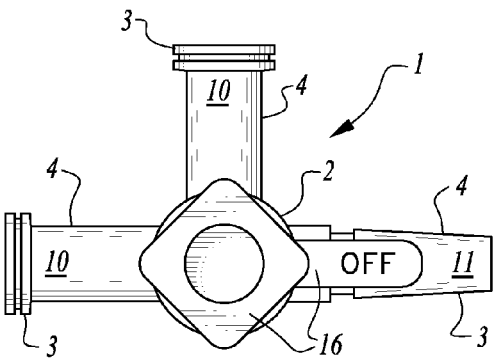
FIG. 1 is a top plan view of a standard prior art stopcock.
Figure 2:
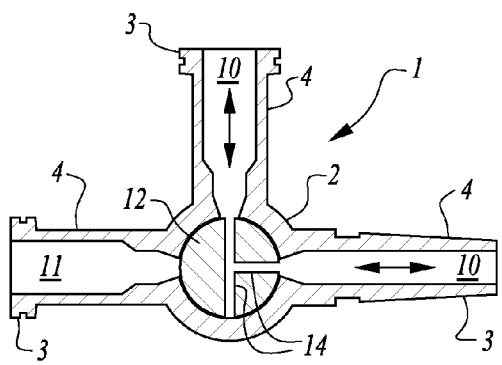
FIGS. 2-5 are full sectional views similar to that which is shown in FIG. 1 and illustrating four different orientations for a central hub of the prior art stopcock, with arrows indicating which ports of the stopcock are open for fluid flow therethrough.
Figure 3:
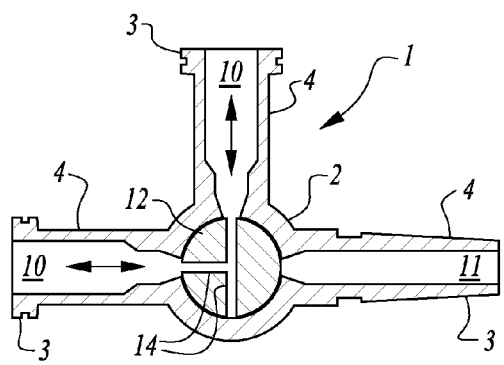
Figure 4:
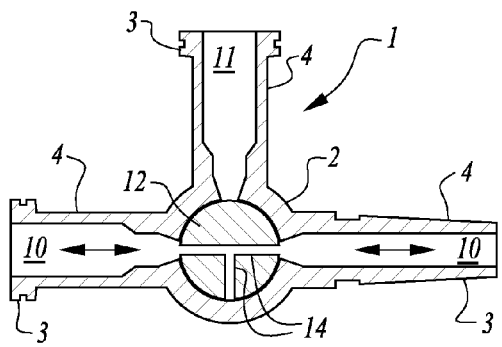
Figure 5:
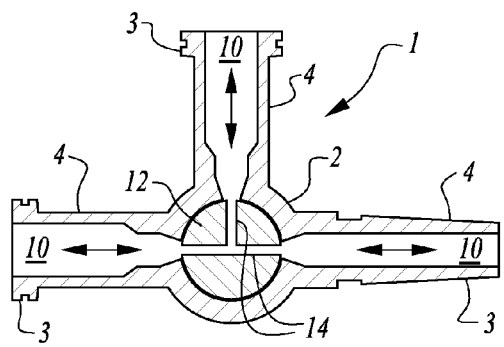
Figure 18:
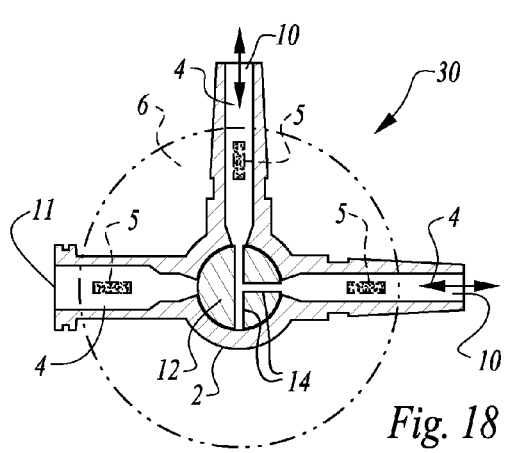
FIGS. 18-23 are top plan views and sectional views of a three way stopcock in various functional states according to this invention.
Figure 19:
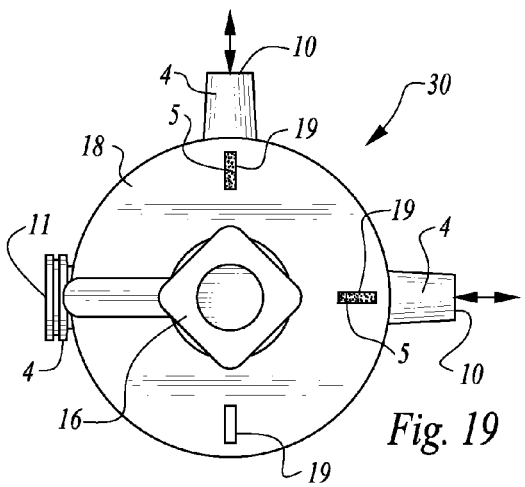
Figure 20:
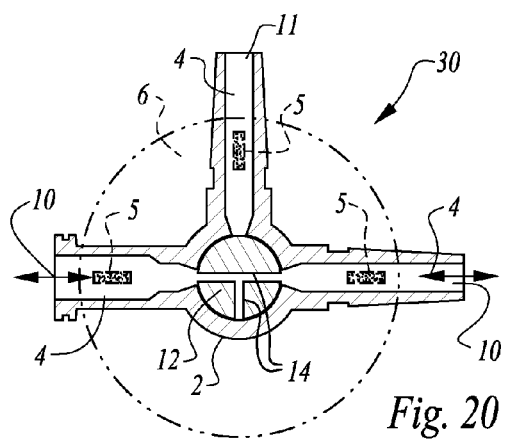
Figure 21:
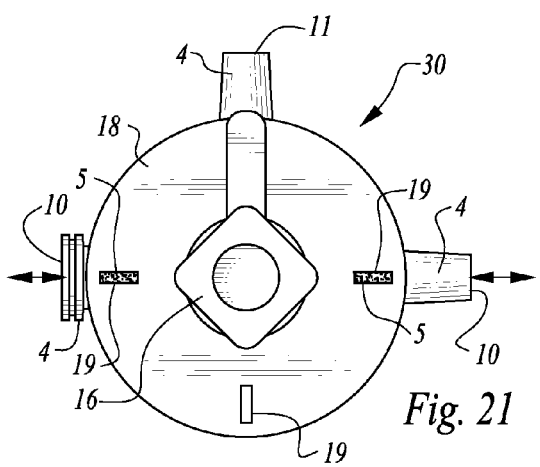
Figure 22:
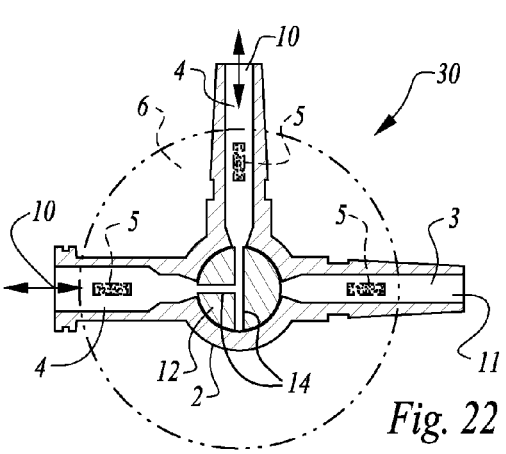
Figure 23:
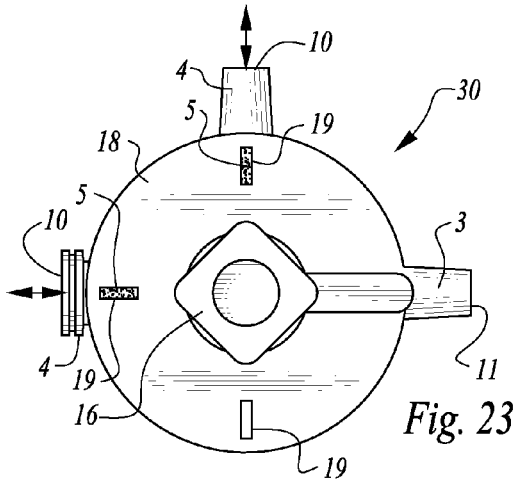
Figure 24:
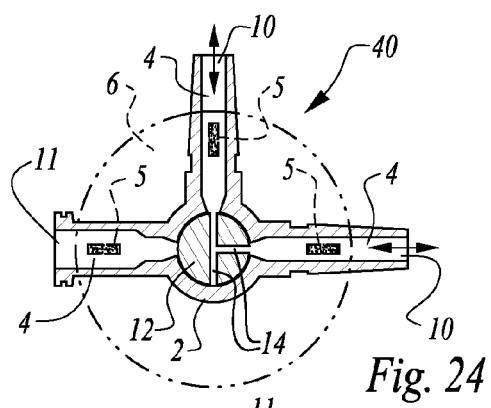
FIGS. 24-31 are top plan views and full sectional views of a four way stopcock in various functional states according to this invention.
Figure 25:
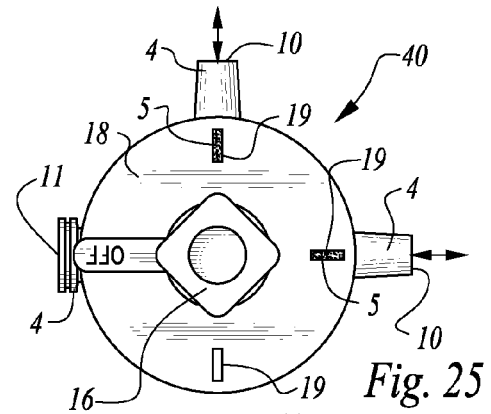
Figure 26:
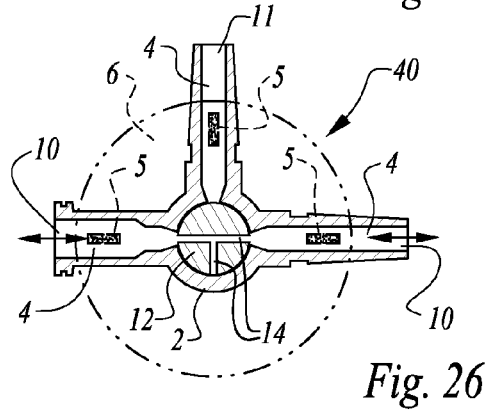
Figure 27:
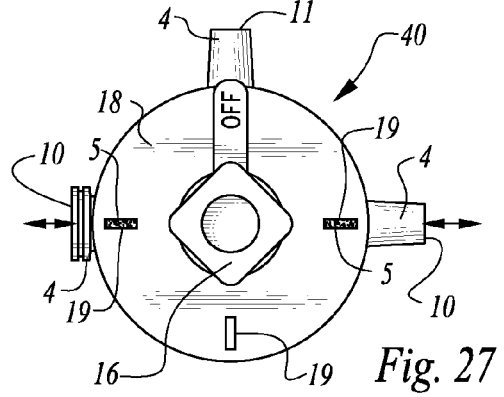
Figure 28:
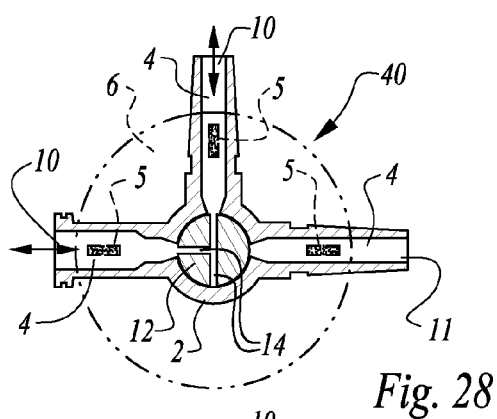
Figure 29:
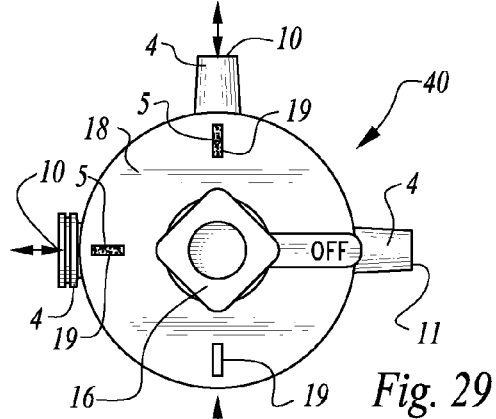
Figure 95:
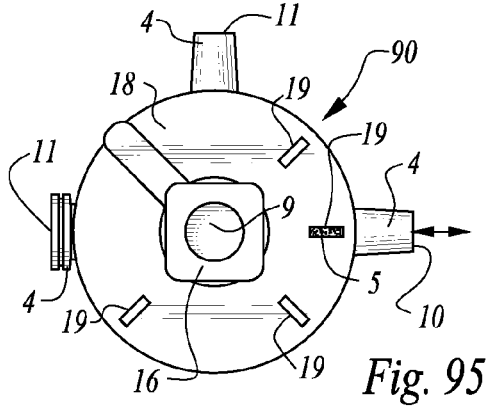

Ports 4 which are closed are provided with the reference numeral 11. Furthermore, open ports are provided with arrows indicative of fluid flow potential through the stopcock 1 (FIGS. 1-95). A central fluid conveyance path 9 (FIGS. 9 and 13) can optionally be provided through the central hub 12. This central fluid conveyance path 9 intersects embedded fluid flow paths 14 within the central hub 12 (FIGS. 18, 20 and 22).

Typically, this central hub 12 is formed along with a central control knob 16 or is configured so that the central control knob 16 can be attached thereto. A pin connector 17 can accommodate such attachment when the knob 16 is on a rear of the valve body 2 (FIGS. 10-13). The embedded flow paths 14 can be formed by drilling or through other forming techniques, such as part of the injection molding process.

To provide the indication of functional state of operation of the stopcock 30 according to a preferred embodiment of this invention (FIGS. 6-13) a pair of plates are provided as indicator portions, including a fixed plate 6 and a rotating fenestrated plate 18. The fixed plate 6 is fixed relative to the valve body 2 and fluid conveyance ports 4. This fixed plate 6 includes markings 5 generally aligned with the fluid conveyance ports 4. The rotating fenestrated plate 18 is configured to block the fixed plate 6 and its markings 5 except where windows/fenestrations 19 in the fenestrated plate 18 are aligned with the embedded fluid flow paths 14 within the central hub 12. At these locations, fenestrations 19 are formed in the rotating fenestrated plate 18 that allow the underlying markings 5 on the fixed plate 6 to be revealed or viewed through the fenestrations 19.

The rotating fenestrated plate 18 rotates with the central hub 12 so that the fenestrations 19 always remain aligned with the embedded fluid flow paths 14 within the central hub 12. When the embedded fluid flow paths 14 are aligned with the fluid conveyance ports 4 in the valve body 2, the fenestrations 19 are automatically aligned with the markings 5 on the fixed plate 6, so that these markings 5 can be seen through the fenestrations 19. These markings 5 can be formed of bright colors or glow in the dark type materials to further enhance the ability of a user to readily see the state of the stopcock 30 (FIGS. 6-13) and thus which ports 4 are currently open.

Figure 8:
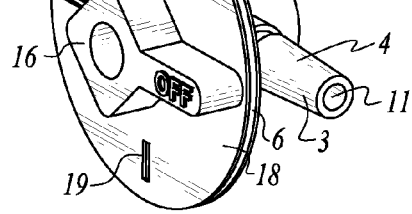
FIG. 8 is a perspective view of that which is shown in FIGS. 6 and 7 with the stopcock shown fully assembled.
Figure 9:
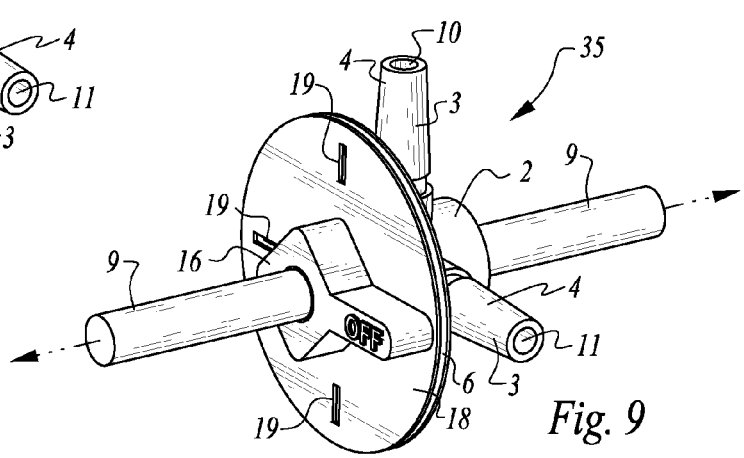
FIG. 9 is a perspective view of an alternative of the stopcock shown in FIGS. 6-8 that additionally includes a central fluid conveyance path extending axially along a rotational axis thereof.
Figure 14:
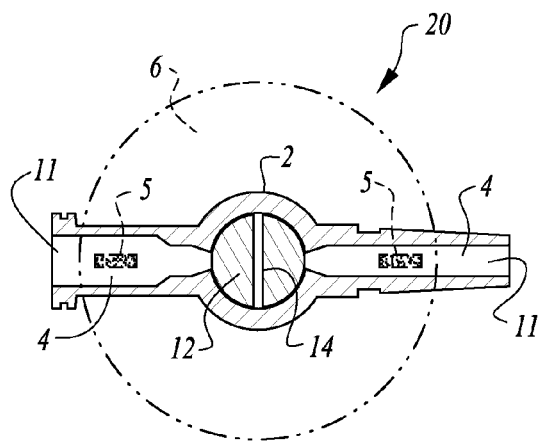
FIGS. 14-17 are top plan views and sectional views of a two way stopcock in various functional states according to this invention.
Figure 15:
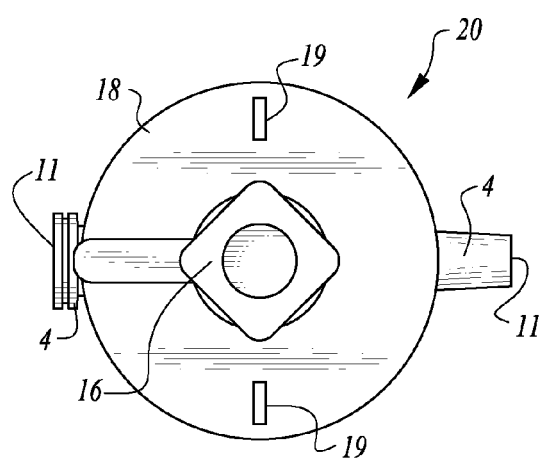
Figure 16:
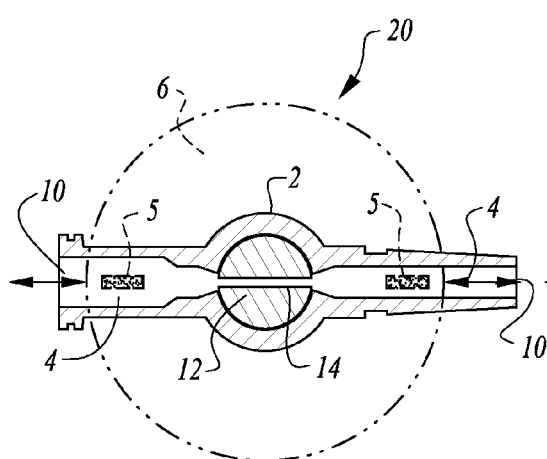
Figure 17:
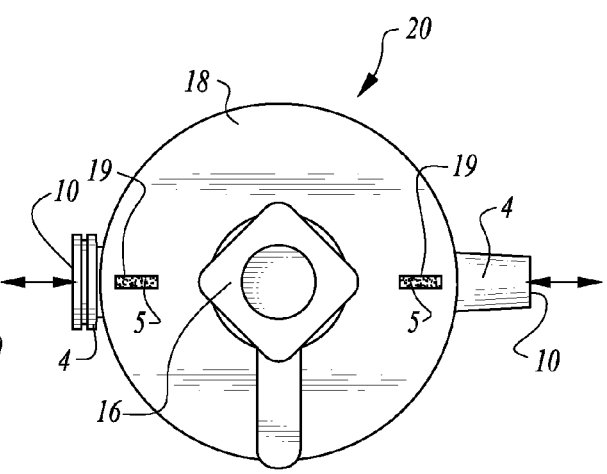

With such a configuration, the stopcock 30 works in a fashion consistent with prior art stopcocks 1, thereby minimizing confusion or misuse. The use involves rotation of the central control knob 16, which rotates the central hub 12 to create open fluid connections between the fluid conveyance ports 4. The additional placement of the rotating fenestrated plate 18 fixed to the central hub 12, and overlying the fixed port identification marks 5 adds the additional clear demarcation of open ports 10 as visualized through the fenestrations 19. The other ports 11 which are closed would not be demarcated as these port identification marks 5 would be covered up by the rotating fenestration plate 18. These closed port identification marks 5 would not be evident as there would be no overlying fenestrations 19 through which they could be viewed. The plates 6,18 can be on either side of the ports 4, as shown in FIGS. 8 and 12. Alternatively, two sets of plates 6, 18 could be provided one on each side of the stopcock 30. Also, two knobs 16, one on each side, could be provided. Although not shown, a fixed gripping area on the stopcock side opposite the knob 16 could also be placed to allow the user's opposite hand to hold the stopcock while the primary hand turns the knob. Such gripping area could be a high friction material on the surface or ribs, bands, etc. that facilitate enhanced gripping.

As rotation of the central hub 12 causes the fenestrations 19 to be aligned with the marks 5, rotation of the central hub 12 also brings the embedded fluid flow paths 14 contained therein into alignment with a desired fluid conveyance ports 4 attached to the periphery of the valve body 2. Thus, the desired open port 10 and closed port 11 configuration determined by the central hub 12 position is created relative to the valve body 2 and its fluid conveyance ports 4.

Optionally, detents can be provided between the central hub 12 and the valve body 2, such as every 30°, 45° or 90° of central hub 12 rotation, or whenever flow paths 14 have ends thereof aligned with ports 4 in the valve body 2, to improve accuracy of positioning of the central hub 12 relative to the valve body 2. Such detents could be formed as teeth and slots formed in the central hub 12 and the recess in the valve body 2 or in other ways consistent with the prior art. Such detents are particularly desirable when more complex stopcock combinations are used.

With particular reference to FIGS. 14-17, details of a two way stopcock 20 are described. This two way stopcock benefits from use of the indicator disks 6, 18, in a simplest stopcock of a two way variety 20. Only when the embedded fluid flow paths 14 are aligned with the ports 4 are the marks 5 aligned with the fenestrations 19 to indicate that fluid flow can occur (FIGS. 16 and 17) through the two way stopcock 20. Otherwise, the marks are blocked by the plate 18 (FIGS. 14 and 15) while in this "off" position.

With particular reference to FIGS. 18-23, details of a three way stopcock 30 are described. With this three way stopcock 30, three ports 4 are provided as shown (note that in all the figures, it is assumed that various different type connector ends (terminiis may be present in various configurations), with two of the ports 180° spaced from each other and one of the ports 90° spaced from each of the other two ports. Correspondingly, fluid flow paths 14 have three ends spaced 90° from each other in a pattern matching that of the ports 4. In this three way stopcock 30, a central hub 12 is only able to rotate 180°. The three operable positions for this central hub 12 relative to the valve body 2 are depicted, with the marks 5 indicating which ports 4 are open by the marks 5 being visible through the fenestrations 19.

Figure 30:
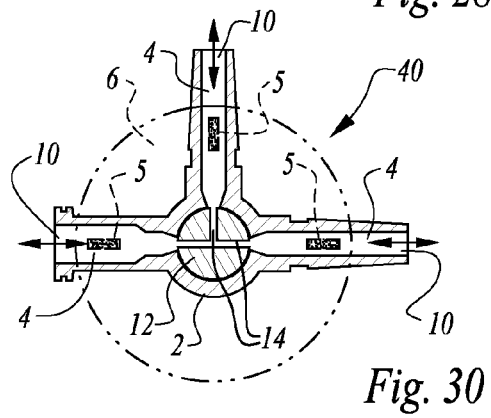
Figure 31:
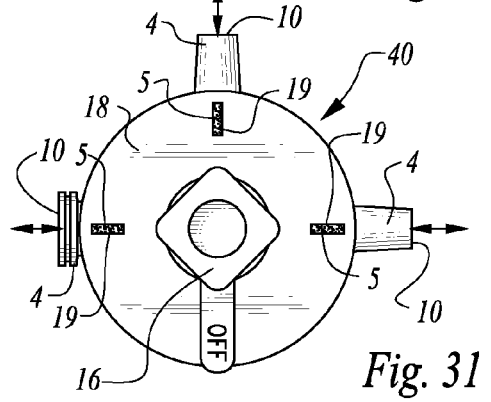

With particular reference to FIGS. 24-31, details of a four way stopcock 40 are described. The four way stopcock 40 is similar in configuration to the three way stopcock 30. However, the central hub 12 is allowed to rotate 360°. Thus, a three way flow option (as depicted in FIGS. 30 and 31) is facilitated with the four way stopcock 40 of FIGS. 24-31. By allowing the central hub 12 and associated embedded flow paths 14 to rotate 360° relative to the valve body 2 and associated fluid conveyance ports 4, a position is facilitated where all three fluid conveyance ports 4 are open to each other simultaneously, as well as the positions described above with respect to the three way stopcock 30 of FIGS. 18-23.

Note from FIGS. 24-31 that the central control knob 14 includes the printing "OFF" thereon. This optional printing and orientation of the central control knob 16 is found in the prior art and thus causes a user to have immediate familiarity with the stopcock 40, should the user have previous experience with prior art stopcocks. However, this printing is somewhat inferential, rather than explicit as to which fluid conveyance ports 4 are open. In particular, this prior art labeling system tells which ports 4 are closed, rather than which ports 4 are open.

With particular reference to FIGS. 32-43, details of a six way stopcock 50 are described according to a first embodiment. With the six way stopcock 50, four fluid conveyance ports 4 are associated with the six way stopcock 50. These four ports 4 are each spaced a similar distance apart from each other, and in a common plane, such that they are substantially 90° from adjacent ports 4. The central hub 12 is configured to include embedded fluid flow paths 14 in a particular configuration to allow for selective opening and closing of the various ports 4 in at least six different configurations.

In particular, the flow paths 14 of this embodiment of the six way stopcock 50, the fluid flow paths 14 following a pattern somewhat similar to the capital letter "K." Four ends are provided for the flow paths 14 and the flow paths are all joined together centrally within the central hub 12. These four ends of the flow paths 14 are at the end of flow path segments that radiate from a center of the central hub 12. Two of these flow path segments are 180° opposite each other. Two additional flow path segments are 90° spaced from each other and 45° spaced from the flow path segments that are oriented 180° away from each other.

Figure 32:
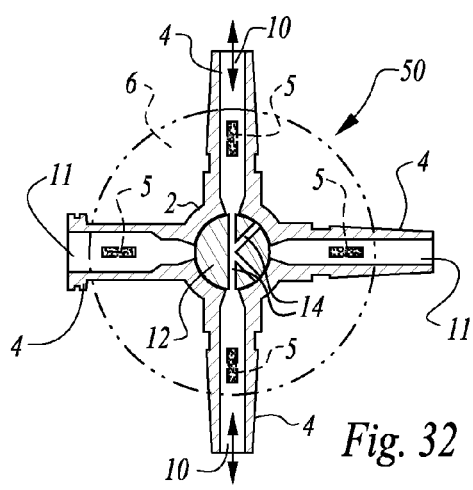
FIGS. 32-43 are top plan views and full sectional views of a six way stopcock in various functional states according to this invention.
Figure 33:
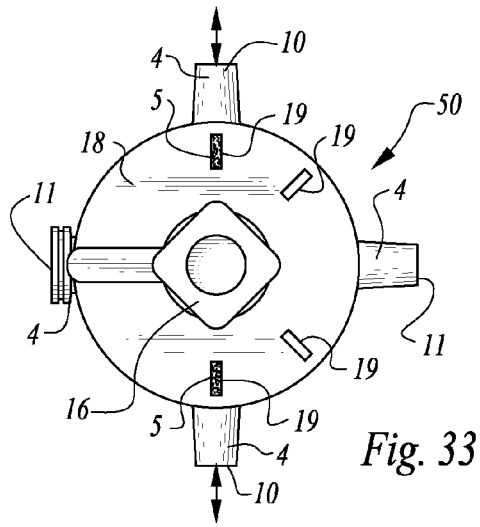
Figure 34:
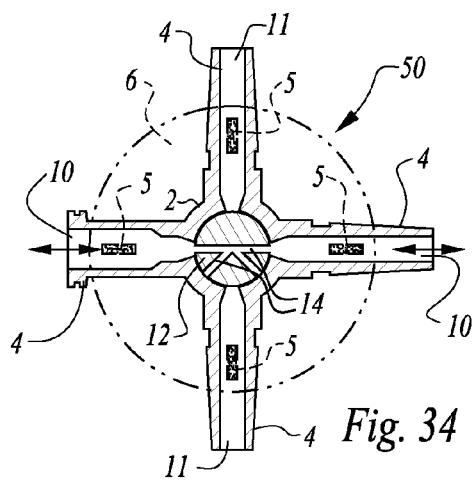
Figure 35:
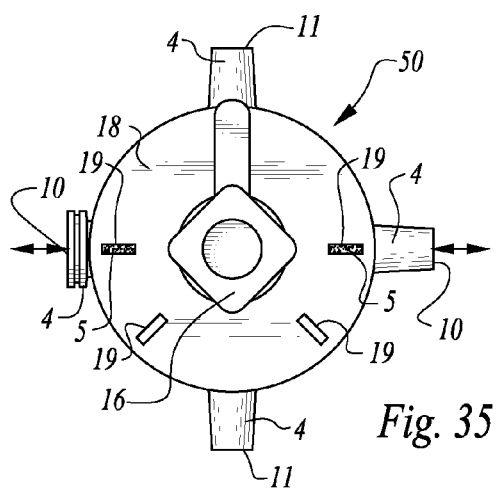

With such a configuration, it can be seen how six different states are provided for the six way stopcock 50, by rotating of the central hub 12 through six different positions, each placed at 45° intervals. A first position is illustrated in FIGS. 32 and 33 which provides two ports 4 opposite each other open (at twelve o'clock and six o'clock positions) and the other two ports opposite each other closed. FIGS. 34 and 35 depict the six way stopcock 50 with the two other ports 4 open (at three o'clock and nine o'clock positions).

Figure 36:
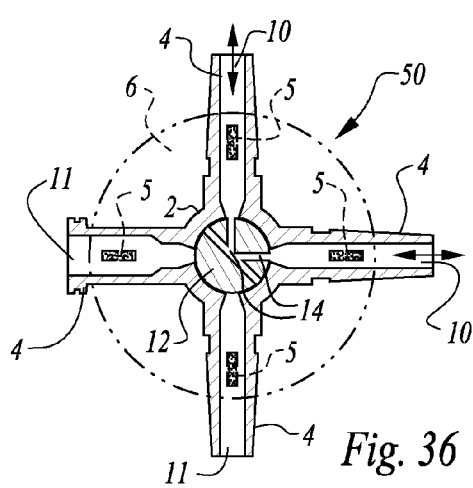
Figure 37:
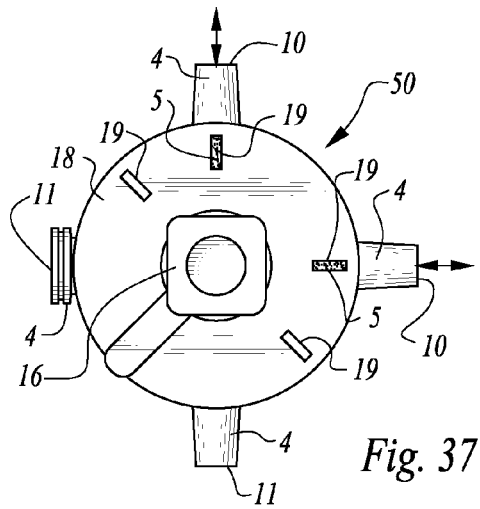
Figure 38:
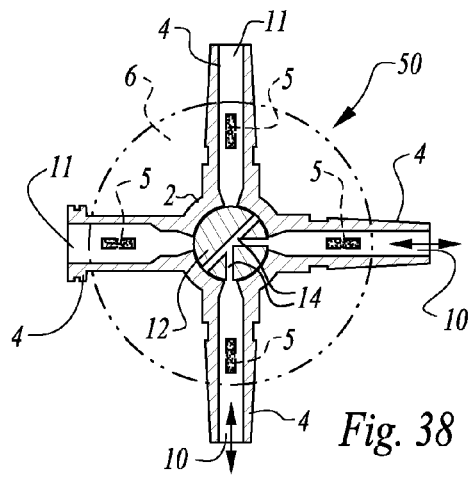
Figure 39:
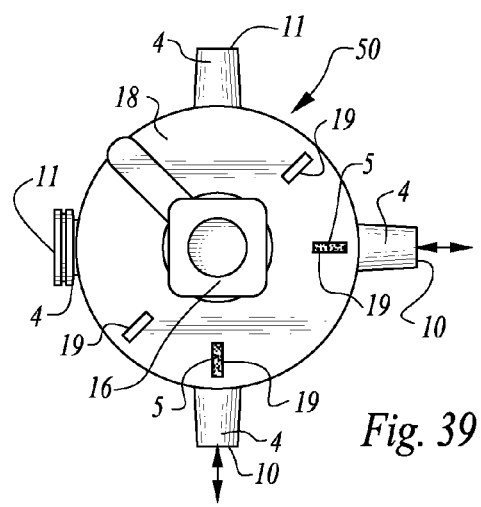
Figure 40:
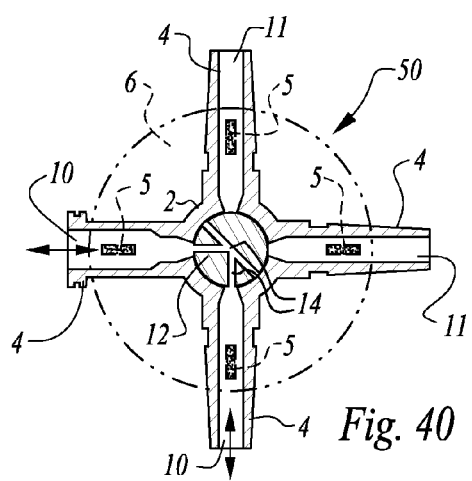
Figure 41:
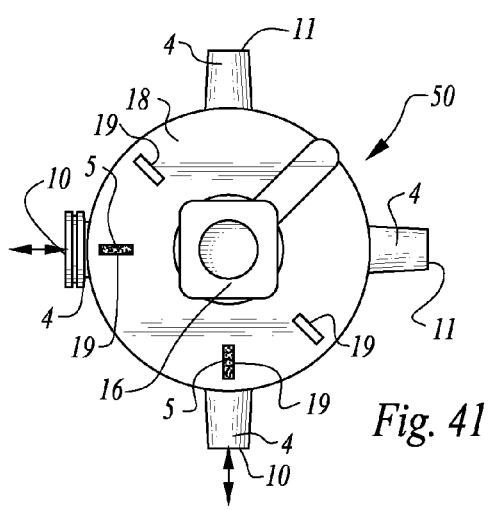
Figure 42:
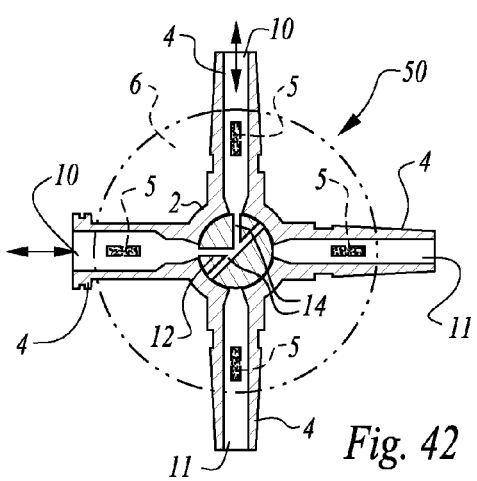
Figure 43:
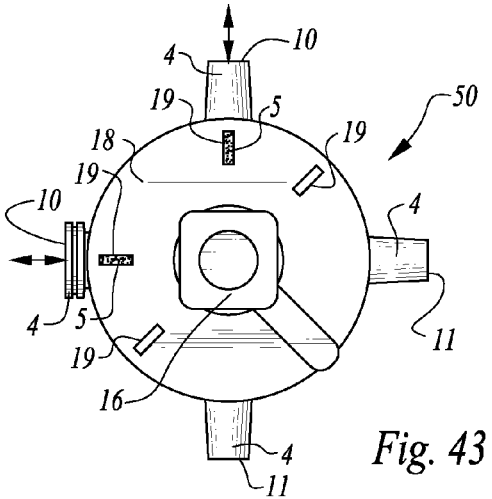
Figure 44:
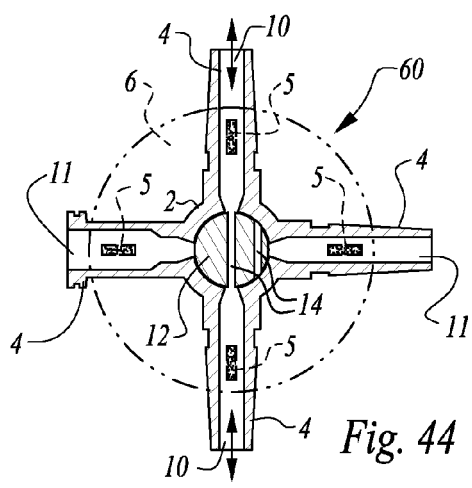
FIGS. 44-55 are top plan views and full sectional views of a first alternative six way stopcock in various functional states according to this invention
Figure 45:
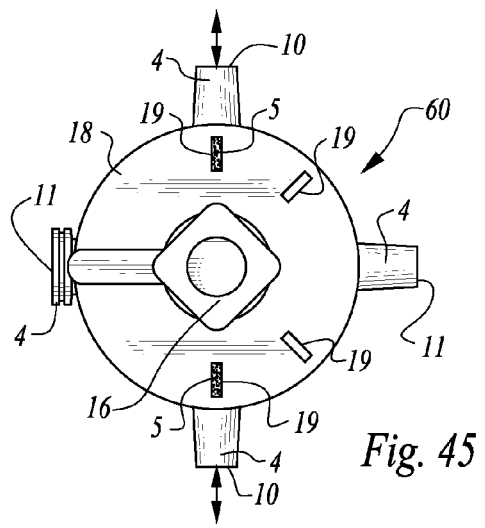
Figure 46:
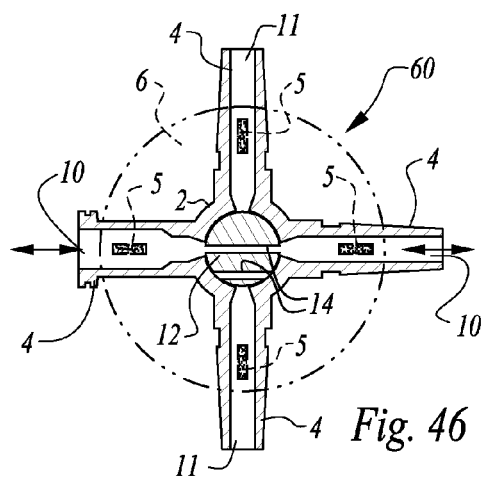
Figure 47:
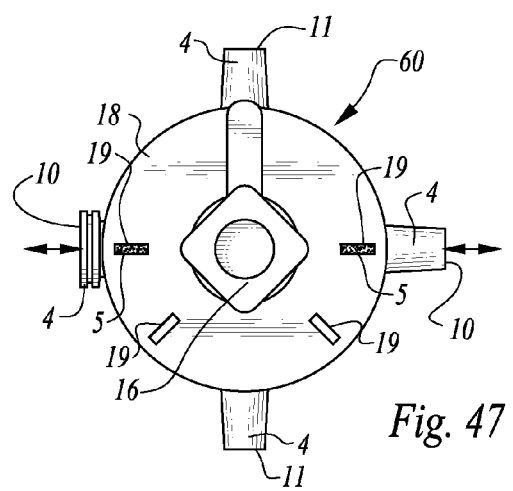
Figure 48:
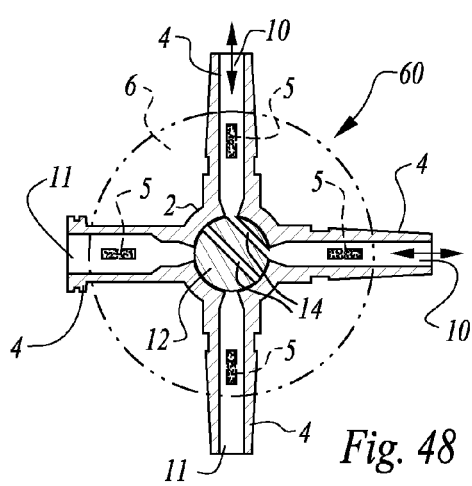
Figure 49:
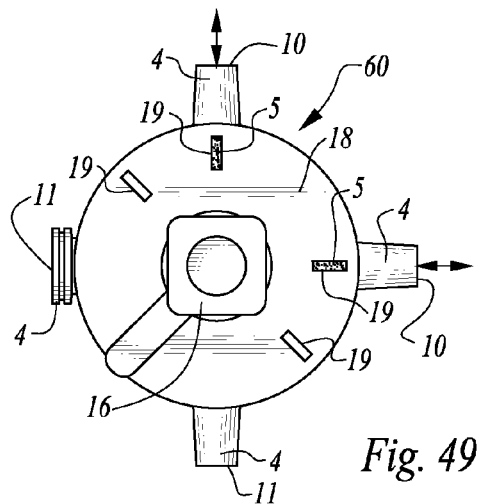
Figure 50:
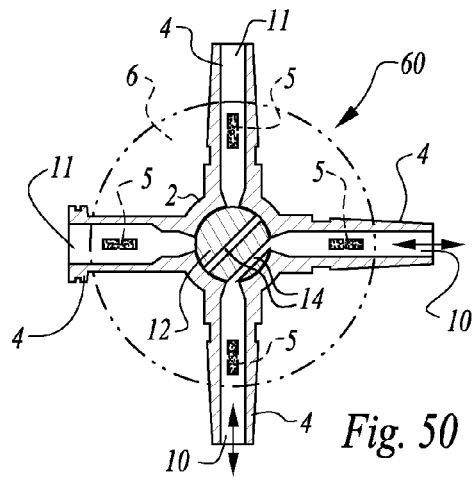
Figure 51:
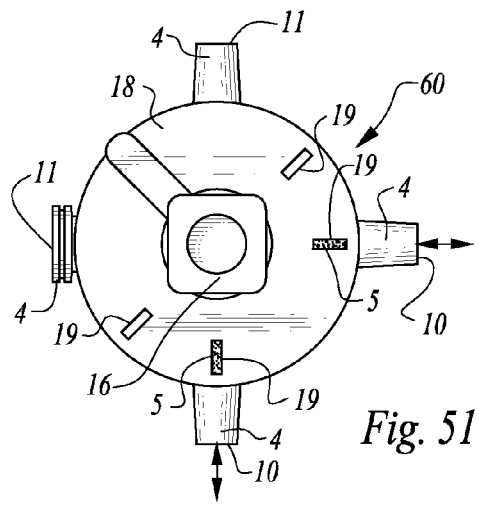
Figure 52:
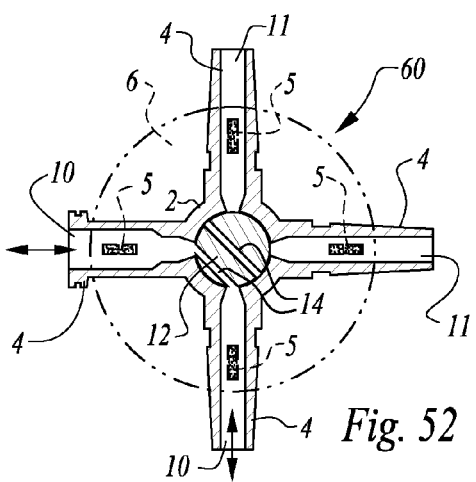
Figure 53:
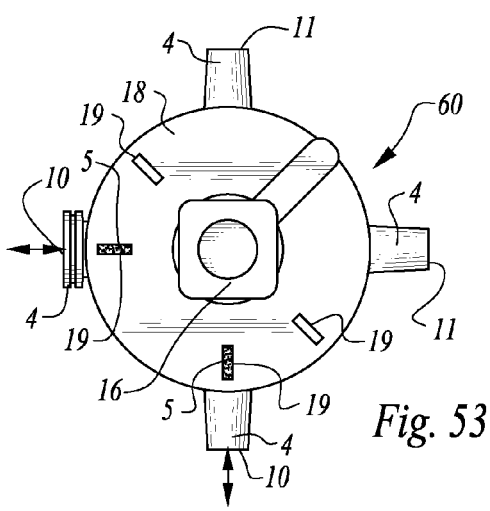
Figure 54:
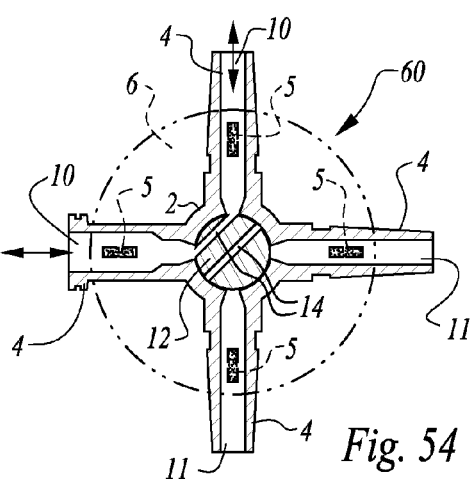
Figure 55:
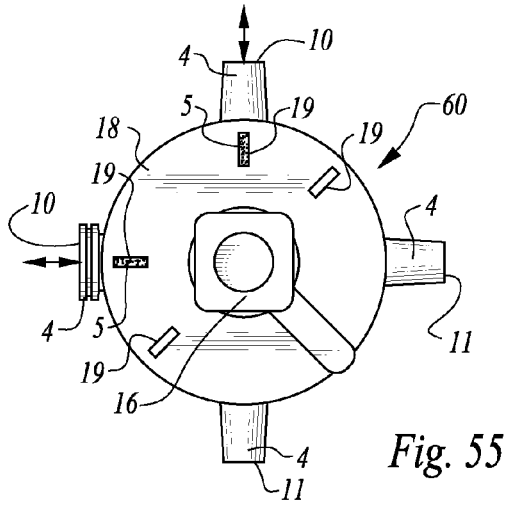
Figure 56:
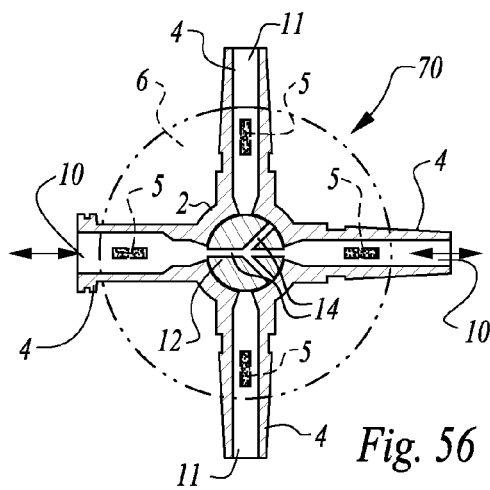
FIGS. 56-67 are top plan views and full sectional views of a second alternative six way stopcock in various functional states according to this invention.
Figure 57:
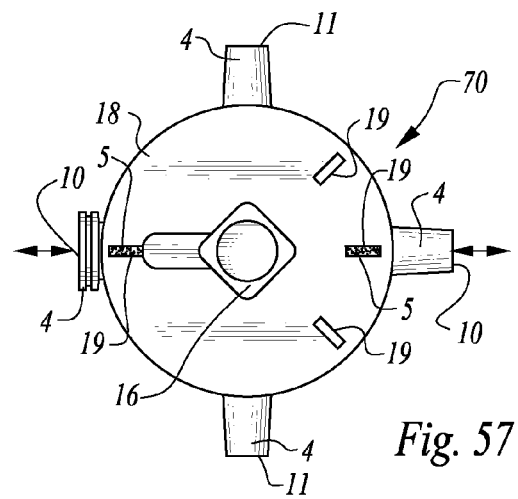
Figure 58:
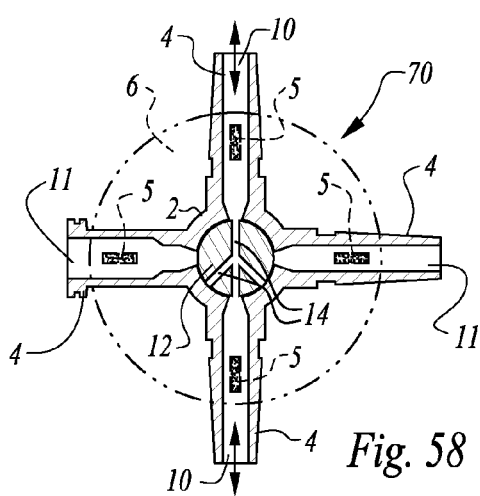
Figure 59:
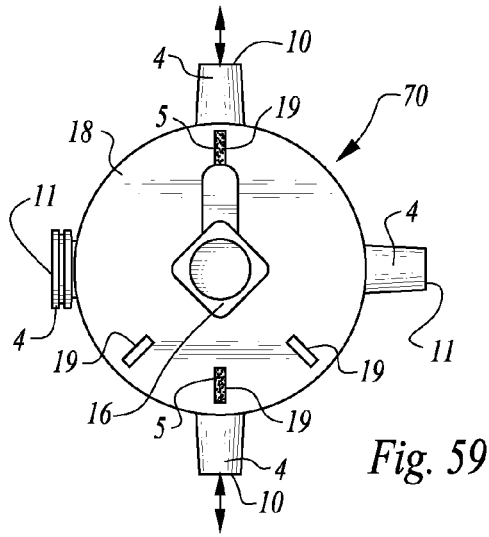
Figure 60:
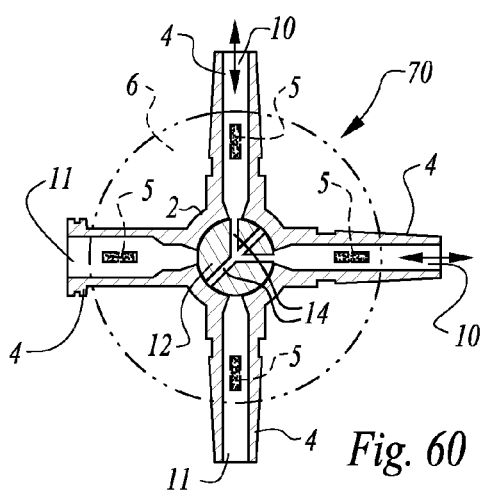
Figure 61:
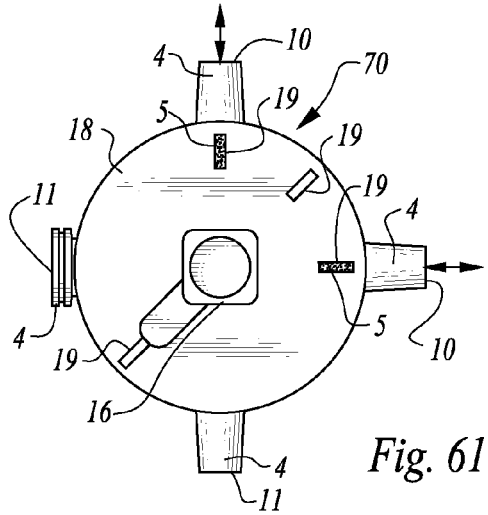
Figure 62:
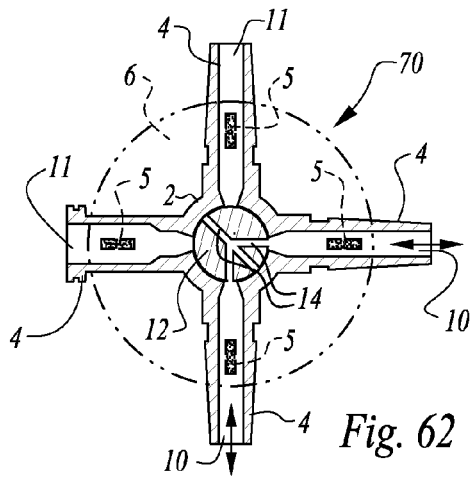
Figure 63:
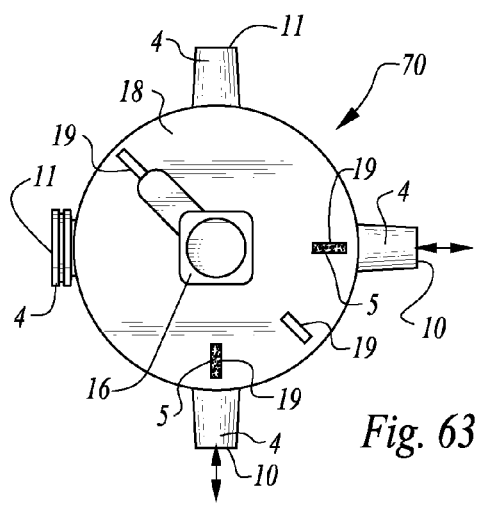
Figure 64:
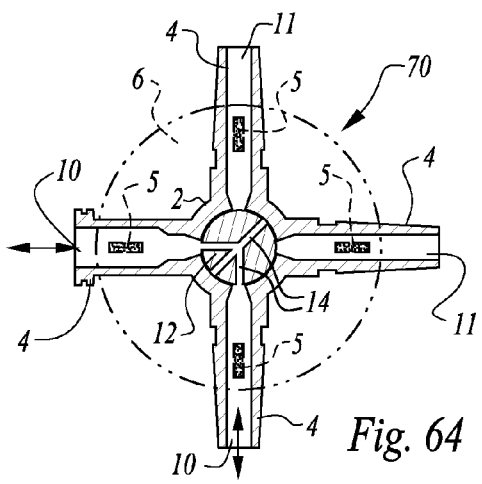
Figure 65:
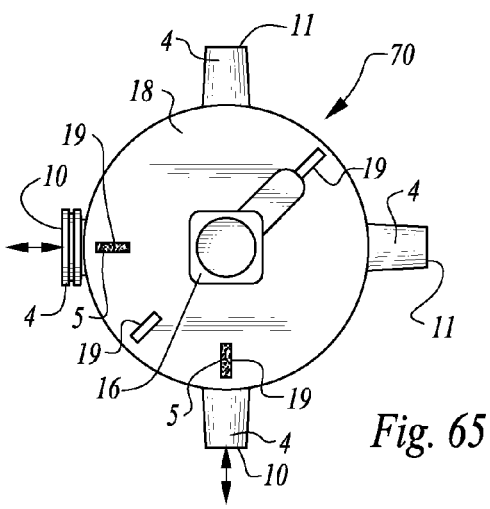
Figure 66:
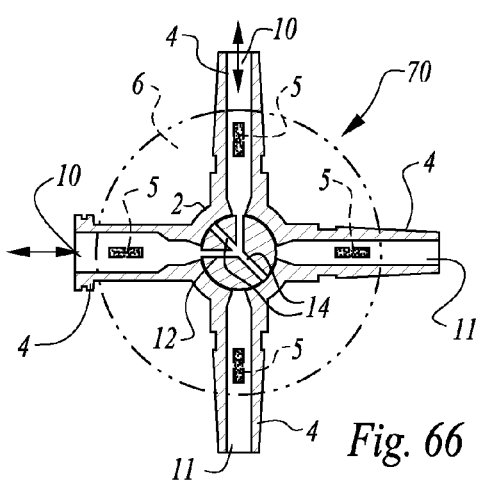
Figure 67:
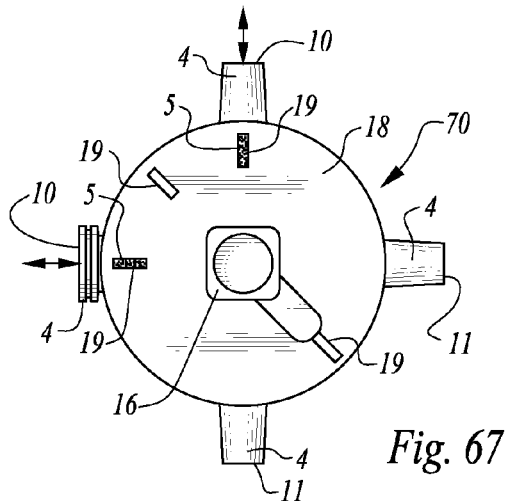
Figure 68:
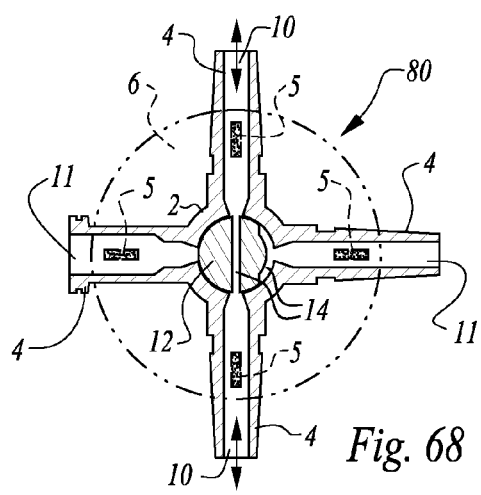
FIGS. 68-79 are top plan views and full sectional views of a third alternative six way stopcock in various functional states according to this invention.
Figure 69:
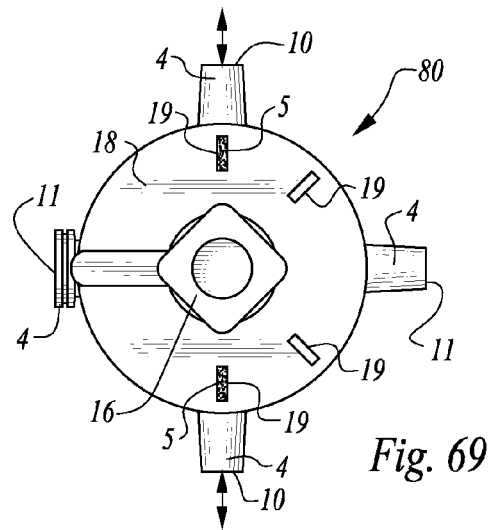
Figure 70:
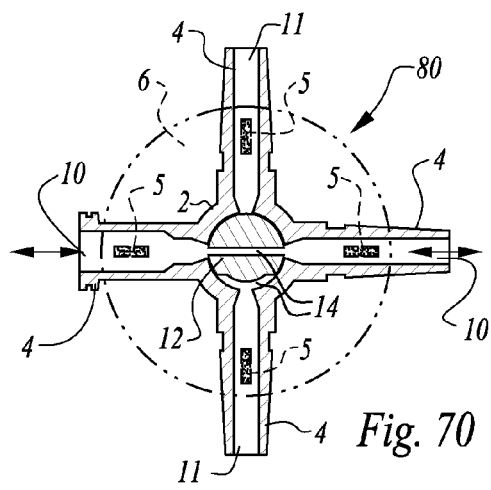
Figure 71:
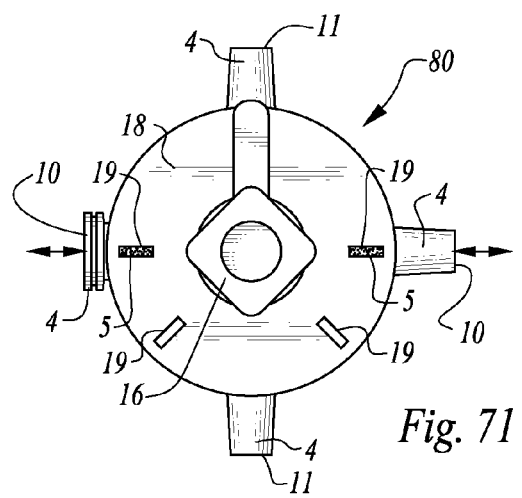
Figure 72:
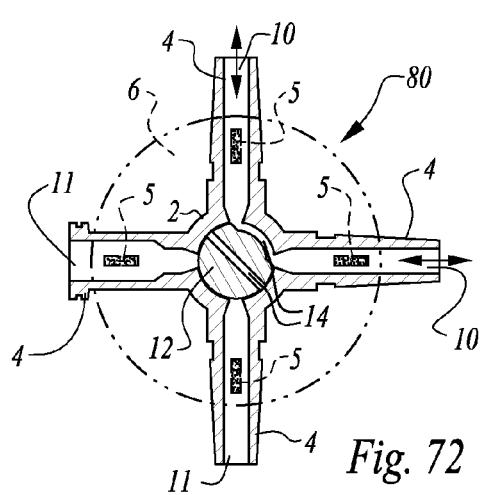
Figure 73:
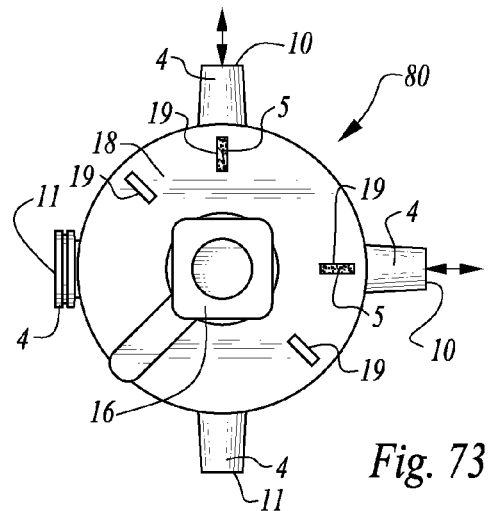
Figure 74:
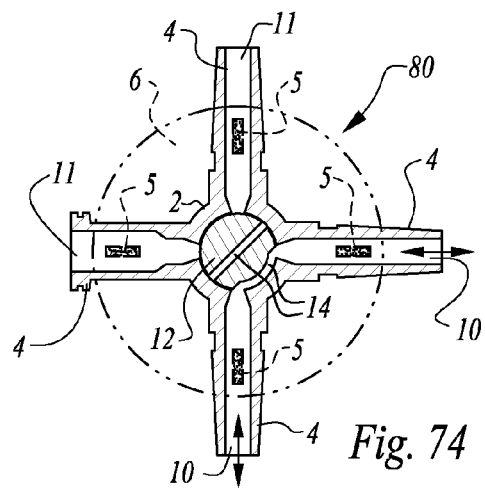
Figure 75:
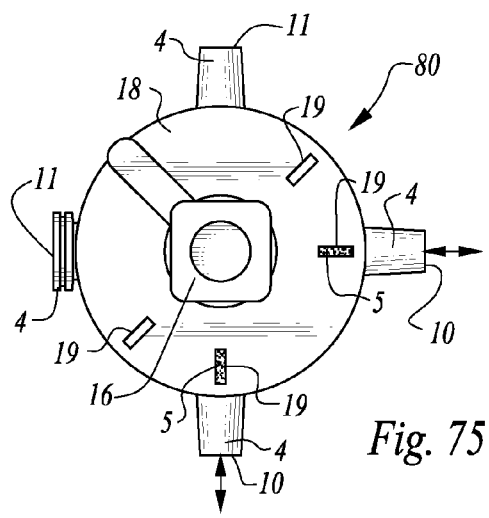
Figure 76:
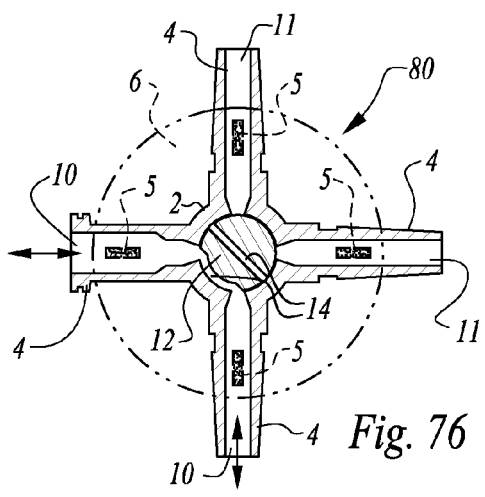
Figure 77:
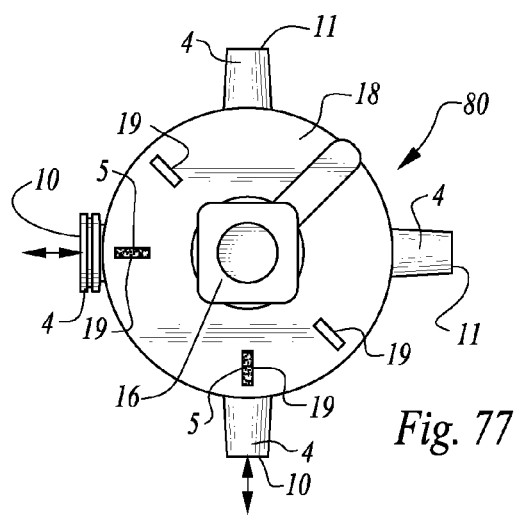
Figure 78:
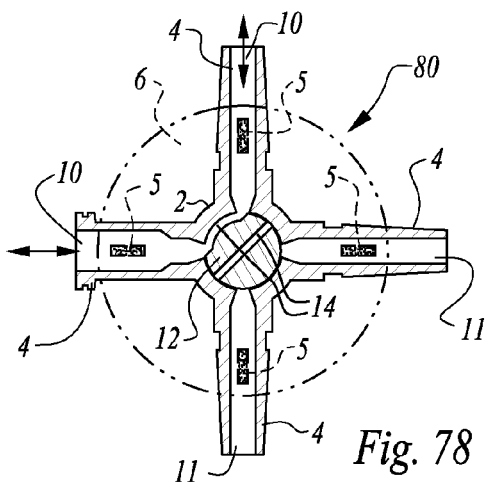
Figure 79:
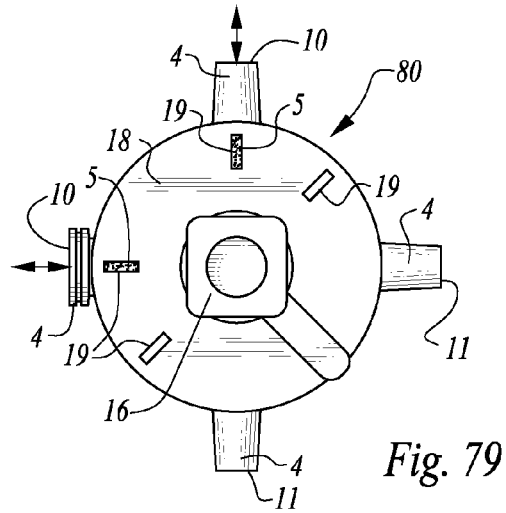

In a third state, the six way stopcock 50 is depicted in FIGS. 36 and 37 with two adjacent ports 4 at a twelve o'clock position and a three o'clock position open, with other positions closed. In FIGS. 38 and 39 the six way stopcock 50 is depicted with ports 4 at the three o'clock and six o'clock position open. In FIGS. 40 and 41 a state of the six way stopcock 50 is depicted where ports 4 at the six o'clock and nine o'clock position are open. In FIGS. 42 and 43 the six way stopcock 50 is shown in a state where ports 4 at the nine o'clock and twelve o'clock position are open.

As with other embodiments, optionally a central control knob 16 can have an axial central fluid path extending through a middle of the central hub 12 and in fluid communication with the flow paths 14 embedded within the central hub 12.

With particular reference to FIGS. 44-55, a first alternative six way stopcock 60 is described. This first alternative six way stopcock 60 has similar functionality to the functionality of the first six way stopcock 50 shown in FIGS. 32-43. However, fluid flow paths 14 are embedded differently within the central hub 12. In particular, two separate flow paths 14 are provided with one passing linearly through a center of the central hub 12. A second fluid flow path is provided parallel with the first fluid flow path and laterally spaced from the first fluid flow path so that ends of the second fluid flow path are spaced 90° away from each other about a central rotational axis of the central hub 12. The various positions and functional states for the first alternative six way stopcock 60 are depicted in pairs of figures laterally spaced from each other from FIGS. 44-55.

Referring to FIGS. 56-67, a second alternative six way stopcock 70 is described. The second alternative six way stopcock 70 has functionality similar to that of the first six way stopcock 50 and first alternative six way stopcock 60, but utilizing fluid flow paths 14 having a different configuration. In particular, the fluid flow paths 14 associated with the second alternative six way stopcock 70 include four separate fluid flow path segments extending from a central axis of the central hub 12 to separate ends at a perimeter of the central hub 12. Two of these ends are spaced 180° from each other. A third and fourth end are each spaced 45° on either side of one of the ends which are 180° opposed from each other. Through rotation of the central hub 12, six different positions are provided similar to those described in detail above with respect to the first six way stopcock 50 and first alternative six way stopcock 60.

FIGS. 68-79 depict a third alternative six way stopcock 80. This third alternative six way stopcock has functionality similar to that described above respect to the first six way stopcock 50, first alternative six way stopcock 60 and second alternative six way stopcock 70. However, the fluid flow paths 14 are configured slightly differently. In particular, the third alternative six way stopcock 80 has fluid flow paths 14 similar to those associated with the first alternative six way stopcock 60 (FIGS. 44-55) except that one of the two fluid flow paths has a curving form following a perimeter of the central hub 12, rather than being linear between ends thereof. The various positions for this third alternative six way stopcock 80 are depicted in FIGS. 68-79.

With particular reference to FIGS. 80-95, details of an eight way stopcock 90 are described. The eight way stopcock 90 includes three fluid conveyance ports 4 generally similar to the fluid conveyance ports 4 associated with the three way stopcock 30 and four way stopcock 40 (FIGS. 18-31). In addition, the eight way stopcock 90 includes an axial central fluid path 9 extending along a central rotational axis of the central hub 12. To cause the eight way stopcock 90 to have eight different positions, fluid flow paths 14 within the central hub 12 have a unique configuration depicted in FIGS. 80-95. In particular, these fluid flow paths are in the form of flow path segments extending radially from a center of said central hub 12 to separate ends. A center of the central hub is preferably enlarged slightly to facilitate axial fluid flow through the central hub 12.

The radial flow path segments include a first two radial flow path segments which are spaced 180° from each other. A third fluid flow path segment extends in a direction perpendicular to the first two fluid flow path segments and spaced 90° away from the first two fluid flow path segments. A fourth fluid flow path segment is located intermediate between the third fluid flow path segment and one of the first two fluid flow path segments and spaced substantially 45° away from said third fluid flow path segment.

Figure 80:
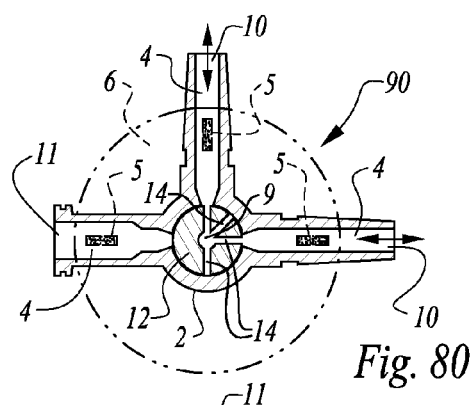
FIGS. 80-95 are top plan views and full sectional views of an eight way stopcock in various functional states according to this invention.
Figure 81:
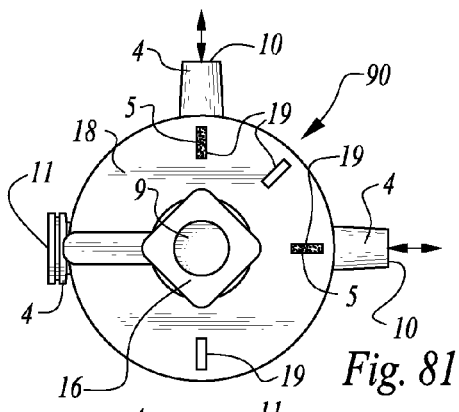
Figure 82:
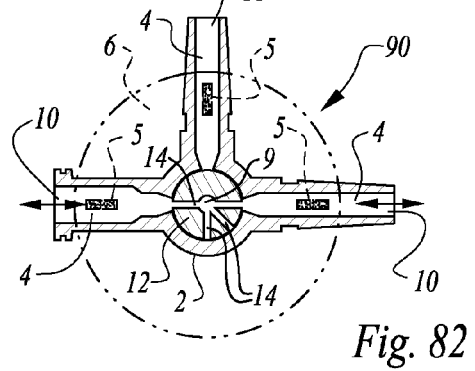
Figure 83:
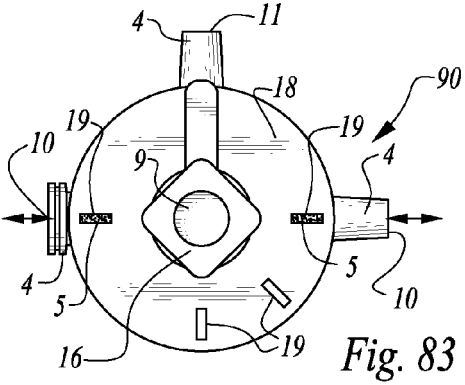
Figure 84:
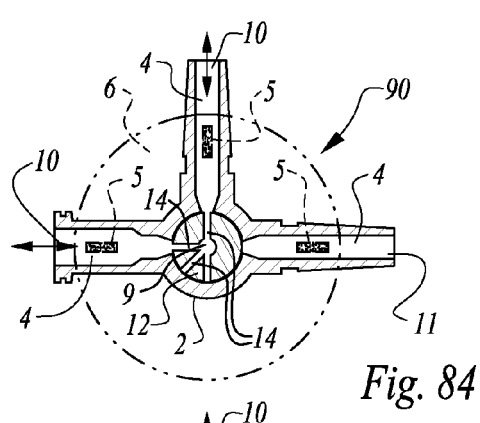
Figure 85:
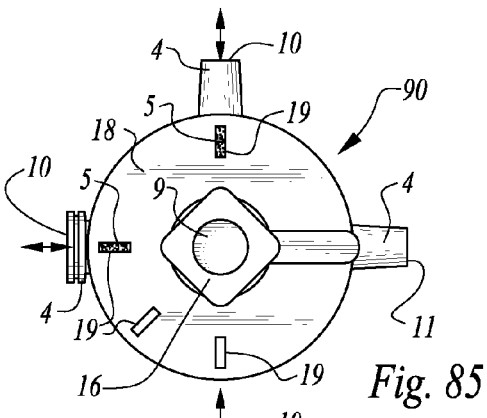
Figure 86:
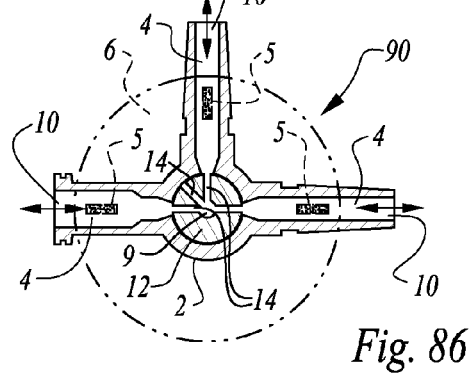
Figure 87:
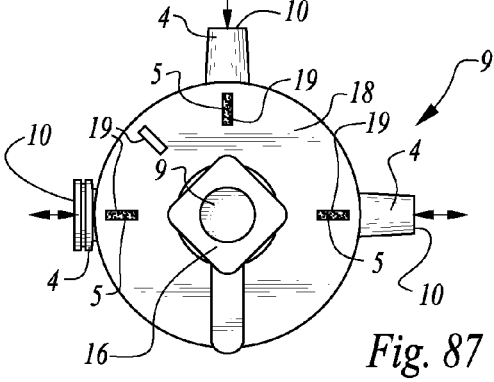

With this configuration, eight different rotational positions and separate functional states are facilitated for the eight way stopcock. A first state is depicted in FIGS. 80 and 81 with two ports 3 at a twelve o'clock and three o'clock position open. FIGS. 82 and 83 display a state of the eight way stopcock 90 where two ports 4 at a three o'clock and a nine o'clock position are open. FIGS. 84 and 85 depict the eight way stopcock 90 in a state where two ports 4 at a nine o'clock and a twelve o'clock position are open. FIGS. 86 and 87 depict a state of the eight way stopcock 90 where three ports 4 at the three o'clock, nine o'clock and twelve o'clock positions are each open.

Figure 88:
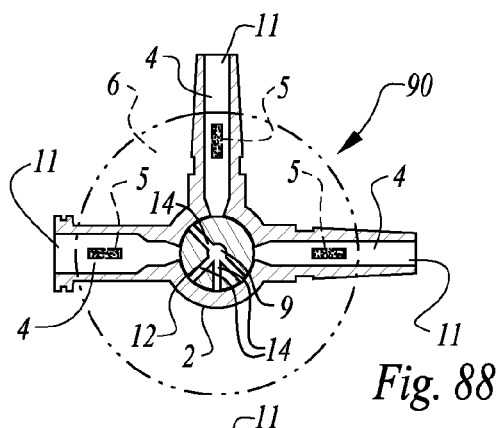
Figure 89:
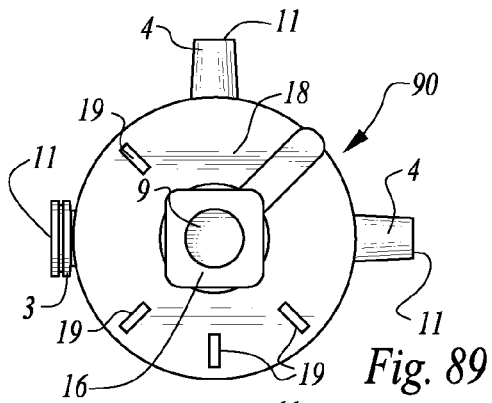
Figure 90:
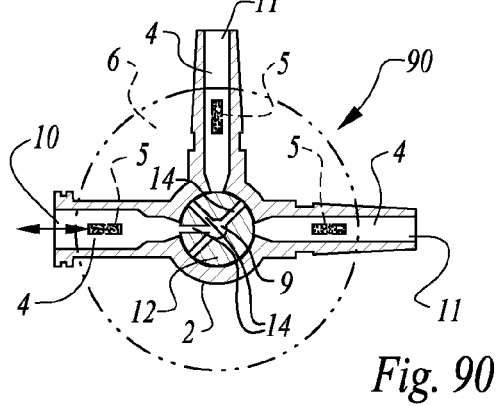
Figure 91:
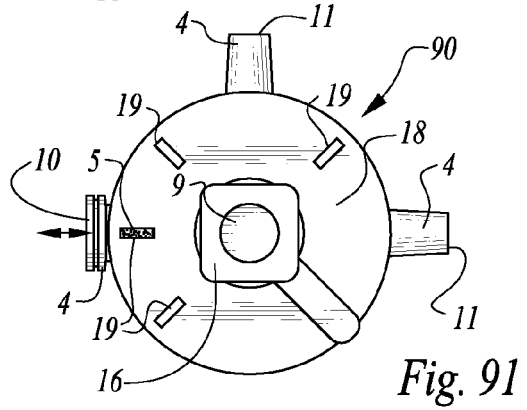

FIGS. 88 and 89 depict a state of the eight way stopcock 90 where none of the ports 4 are open. Note that the axial central fluid path 9 through the central hub 12 is always open to flow through it, but will not necessarily receive flow from the peripheral fluid conveyance ports 4 (the central fluid flow path 9 will only receive flow from a peripheral fluid conveyance port 4 if it is open 10). FIGS. 90 and 91 depict a state of the eight way stopcock 90 where only one of the ports 4 at the nine o'clock position is open. Because the central hub 12 includes an axial fluid path extending therethrough, fluid flow occurs between the port 4 at the nine o'clock position and the axial central fluid path 9.

Figure 92:
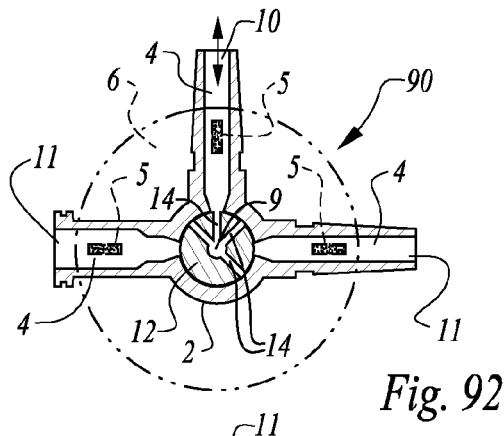
Figure 93:
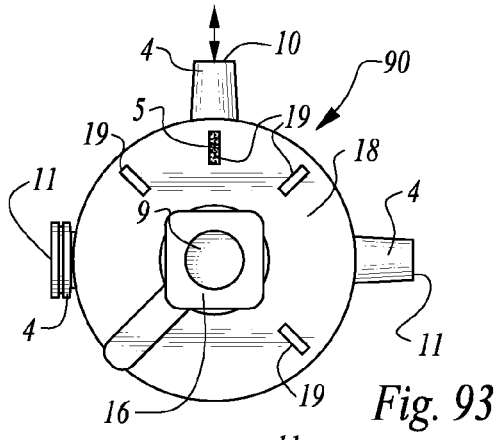
Figure 94:
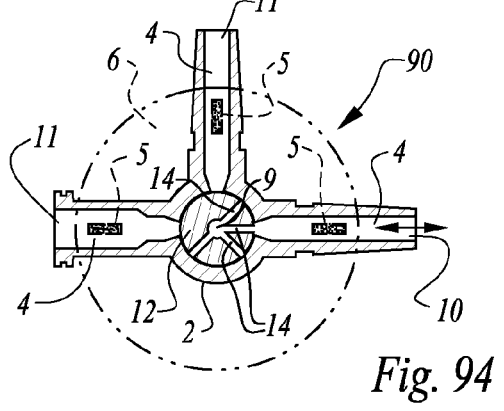

FIGS. 92 and 93 depict an additional state of the eight way stopcock 90 where a single port 4 at a twelve o'clock position is open, along with the axial central fluid path 9. FIGS. 94 and 95 depict an additional state of the eight way stopcock 90 where a single port 4 at a three o'clock position is open, along with the axial central fluid path 9.

When a user is designing a system which has multiple fluid transport lines, such as medical tubing within a patient treatment environment, the use would initially ascertain the number of different tubes involved and the number of fluid sources and the number of fluid destinations. This total number of fluid sources and destinations is a first factor in determining which stopcock to utilize. Secondarily, the user can ascertain which separate sources or destinations of fluid need to communicate directly together. The user then selects one of the stopcocks having the desired degree of operability and connects medical tubing between the selected stopcock and each of the sources or destinations of fluid. The user may also connect this invention with its flow designating system in series as a manifold for more connectivity if needed, as is done with the prior art. This invention may also include multiple stopcocks molded together as a single unit manifold as is also seen in the prior art.

Thereafter, as the user needs to have fluid conveyed in different ways through the stopcock between sources and destinations for fluids, the user rotates the central hub 12 until the fixed plate 6 and rotating fenestrated plate 18 are aligned to indicate openness of ports 4 corresponding with desired openness for operation of the overall system (Other optional embodiments may allow the stopcock to indicate which ports are closed, or indicate numbers, letters or symbols as desired by the specific use. For instance, instead of "open" and "closed" valve functional states, the stopcock can indicate flow rates of fluids, or select pressure of the fluids, or other selectable functional states). Later, the user can quickly monitor the stopcock to ensure that it is still positioned properly by verifying that the marks 5 on the fixed plate 6 can still be seen and are in the proper positions viewed through the fenestrations 19 and the rotating fenestrated plate 18. If out of position at all, the user can make appropriate adjustments. When different operational states of the system are required, the central hub 12 is appropriately rotated until the appropriate ports 4 are open or closed to configure the system for the new operational status.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A stopcock with intuitive functional state display identifying flow through the stopcock, the stopcock comprising in combination:
a valve body having a recess;
at least two fluid pathways joined to said valve body;
each fluid pathway adapted to route fluid into and out of said valve body;
a central manifold located within said recess of said valve body;
said central manifold including a knob grippable by fingers of a user, said central manifold adapted to be rotated relative to said valve body through said knob;
said central manifold having at least one multi-ended flow path therein;
said central manifold having ends of said at least one multi-ended flow path selectively alignable with various ones of said at least two fluid pathways of said valve body;
a first indicator portion fixed relative to said valve body and having markings thereon;
a second indicator portion separate from said knob and coupled to said central manifold and overlying said first indicator portion;
said second indicator portion adapted to rotate when said central manifold rotates;
said first indicator portion and said second indicator portion interacting to display said markings indicative of a functional state of said stopcock;
wherein said first indicator portion includes at least one of said markings adjacent each fluid pathway;
said second indicator portion including an object configured to block all of said markings of said first indicator except those markings which are adjacent fluid pathways of said valve body which are open through said central manifold;
wherein said second indicator portion includes a surface with windows therein, said windows located adjacent to the ends of said at least one multi-ended flow path of said central manifold, such that when said ends of said flow paths of said central manifold are aligned with said fluid pathways of said valve body, said markings of said first indicator portion are aligned with said windows of said second indicator portion and can be visualized through said surface of said second indicator portion;
wherein said first indicator portion includes a plate with said markings thereon, said plate located adjacent said surface of said second indicator portion; and
wherein said first indicator portion and said second indicator portion are in the form of thin parallel plates.

2. The stopcock of claim 1 wherein said valve body recess and said central manifold have a matching cylindrical form, said first indicator plate having a central circular hole through which said valve body extends.

3. The stopcock of claim 1 wherein said plate of said first indicator portion and said surface of said second indicator portion are both located on a side of said valve body having said knob of said central manifold.

4. The stopcock of claim 1 wherein said stopcock includes a finger grip fixed to said valve body on a side opposite said knob, such that a user can apply counter torque when rotating said knob.

5. The stopcock of claim 1 wherein said central manifold includes an axial flow path extending along a rotational axis of said central manifold, said axial flow path intersecting at least one of said multi-ended flow paths within said central manifold which extend to said ends of said central manifold, such that an additional flow pathway axially through said stopcock is facilitated.

6. The stopcock of claim 1 wherein said valve body includes two fluid pathways extending radially from said valve body substantially perpendicular to a rotational axis of said central manifold and spaced from each other approximately 180°, said central manifold including a single flow path extending radially to opposing ends spaced 180° away from each other, said two ends of said flow path within said central manifold adapted to be selectively aligned with said two fluid pathways of said valve body.

7. The stopcock of claim 6 wherein said valve body includes three fluid pathways each oriented within a common plane substantially perpendicular to a rotational axis of said central manifold, two of said three fluid pathways oriented substantially 180° away from each other and one of said fluid pathways oriented substantially 90° away from each of the other of said three fluid pathways; and
said central manifold including three ends of said flow path open to each other, two of said ends oriented 180° away from each other and one of said ends oriented 90° away from the other two ends, said ends of said central manifold adapted to be aligned with said fluid pathways of said valve body in at least four configurations including a first configuration with all three ends of said central manifold aligned with all three fluid pathways of said valve body, a second orientation with two 180° spaced ends of said central manifold aligned with two 180° opposed fluid pathways of said valve body, and third and fourth orientations with different adjacent pairs of said ends of said central manifold aligned with different adjacent pairs of said fluid pathways of said valve body.

8. The stopcock of claim 1 wherein said valve body includes four fluid pathways oriented in a common plane perpendicular to an axis of rotation of said central manifold, said four fluid pathways each spaced substantially 90° from two adjacent said fluid pathways, said central manifold including four ends of said at least one multi-ended flow path, said four ends including two ends spaced substantially 180° away from each other and two ends spaced substantially 90° away from each other.

9. The stopcock of claim 8 wherein said central manifold includes a circular perimeter with a first embedded fluid flow path extending between two ends spaced 180° from each other, and second and third fluid flow paths intersecting with said first fluid flow path and extending to ends on a common side of said first fluid flow path with said ends of said second and third fluid flow paths spaced 90° away from each other.

10. The stopcock of claim 8 wherein said central manifold includes a circular perimeter with a first flow path extending between first and second ends and a second flow path extending between third and fourth ends, said first flow path having ends spaced 180° from each other, said second flow path having said ends spaced 90° from each other, said second flow path located substantially parallel with said first flow path and spaced laterally from said first flow path.

11. The stopcock of claim 8 wherein said central manifold includes a substantially circular perimeter with a first flow path extending between first and second ends spaced 180° from each other substantially, with a third flow path joined to said first flow path and having an end spaced 45° away from one of said ends of said first flow path, and a fourth flow path joined to said first flow path and having an end spaced 45° away from one of said ends of said first flow path and 90° away from said end of said third flow path, said third flow path and said fourth flow path located on opposite sides of said first flow path.

12. The stopcock of claim 8 wherein said central manifold includes at least two multi-ended flow paths extending between ends thereof, a first one of said at least two flow paths having said ends located 180° from each other and a second one of said at least two flow paths having ends thereof located 90° away from each other and with at least one of said flow paths having a curving form following a circular perimeter of said central manifold between said ends.

13. The stopcock of claim 1 wherein said markings are visually enhanced with pigments taken from the group including bright colored pigments and glow in the dark pigments.

14. The stopcock of claim 1 wherein said stopcock is attached in series with at least one other similar stopcock to form a multi-stopcock manifold.

15. A valve, comprising,
a valve body having an inner recess;
first, second, and third ports coupled to the valve body, each of the first, second, and third ports in fluid communication with the inner recess of the valve body, the first port and the third port disposed along a common line extending through the valve body, and the second port coupled to the valve body at a position centered between the first port and the third port;
a central hub having embedded flow paths, the central hub defined to fit within the inner recess of the valve body;
a first indicator portion fixedly disposed to the valve body;
a knob coupled to the central hub to enable rotation of the central hub within the valve body, such that rotation moves the embedded flow paths into flow communication with selected ones of the first, second, and third ports;
a second indicator portion separate from the knob and fixed relative to the knob, such that rotation of the knob rotates the second indicator portion, the second indicator portion disposed proximate to the first indicator portion; and
wherein the first and second indicator portions are configured to together display markings that identify a current open orientation of the embedded flow paths relative to the first, second and third ports.

16. The valve of claim 15 wherein the knob includes a portion having a designation thereon, the designation indicating that a port is closed;
wherein when the portion of the knob having the designation thereon is aligned with one of the first, second, or third ports, the port with which the portion of the knob having the designation thereon is aligned is closed and the other two ports of the first, second, and third ports are open; and
wherein when the portion of the knob having the designation thereon is aligned opposite the second port of the valve body, each of the first, second, and third ports is open.

17. The valve of claim 16 wherein the portion of the knob has the designation "OFF" provided thereon.

18. The valve of claim 16 wherein the first and second indicator portions comprise a pair of plates with markings on one of the plates and windows on one of the plates.

19. The valve of claim 15 wherein at least one fluid pathway of the valve is open between at least two of the ports whenever the portion of the knob having the designation thereon is in one of four primary positions, the four primary positions including a first primary position in which the portion of the knob having the designation thereon is aligned with the first port, a second primary position in which the portion of the knob having the designation thereon is aligned with the second port, a third primary position in which the portion of the knob having the designation thereon is aligned with the third port, and a fourth primary position in which the portion of the knob having the designation thereon is aligned opposite the second port of the valve body.

20. The valve of claim 15 wherein the knob is fixed to the central hub, the knob having an elongate form extending perpendicular to a rotational axis of the central hub to tend to point along a line parallel with the elongate form of the knob and away from the rotational axis, the designation located upon the knob.

21. The valve of claim 15 wherein when the knob extends to a primary position which does not include one of the ports, all of the embedded flow paths are aligned with one of the ports for common flow between all ports.

* * * * *